(12) United States Patent
Seki et al.

(10) Patent No.: US 9,682,915 B2
(45) Date of Patent: Jun. 20, 2017

(54) METHOD FOR PRODUCING METHACRYLIC ACID ESTER

(71) Applicant: SUMITOMO CHEMICAL COMPANY, LIMITED, Tokyo (JP)

(72) Inventors: Kohei Seki, Niihama (JP); Tetsuya Suzuta, Niihama (JP); Naoki Miura, Ichihara (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 0 days.

(21) Appl. No.: 14/780,232

(22) PCT Filed: Mar. 19, 2014

(86) PCT No.: PCT/JP2014/058707
§ 371 (c)(1),
(2) Date: Sep. 25, 2015

(87) PCT Pub. No.: WO2014/157432
PCT Pub. Date: Oct. 2, 2014

(65) Prior Publication Data
US 2016/0039738 A1 Feb. 11, 2016

(30) Foreign Application Priority Data

Mar. 26, 2013 (JP) .................. 2013-063491

(51) Int. Cl.
C07C 67/38 (2006.01)
C07C 1/24 (2006.01)
C07C 5/25 (2006.01)
C07C 1/207 (2006.01)

(52) U.S. Cl.
CPC ............ *C07C 67/38* (2013.01); *C07C 1/2076* (2013.01); *C07C 1/24* (2013.01); *C07C 5/2506* (2013.01); *C07C 2521/04* (2013.01); *C07C 2521/08* (2013.01); *C07C 2523/04* (2013.01); *Y02P 20/582* (2015.11)

(58) Field of Classification Search
None
See application file for complete search history.

(56) References Cited

U.S. PATENT DOCUMENTS

| | | | | | |
|---|---|---|---|---|---|
| 4,301,319 | A | * | 11/1981 | Greene | ...................... C07C 1/24 585/638 |
| 2004/0102647 | A1 | * | 5/2004 | Everett | ...................... C07C 1/24 562/532 |
| 2009/0209782 | A1 | * | 8/2009 | Mizuno | ................... C07C 67/38 560/205 |
| 2011/0046417 | A1 | | 2/2011 | Kawamura et al. | |

FOREIGN PATENT DOCUMENTS

| | | |
|---|---|---|
| CN | 87101272 A | 7/1988 |
| CN | 101415669 A | 4/2009 |
| EP | 0272662 A2 | 6/1988 |
| JP | 63-233931 A | 9/1988 |
| JP | 2007-269707 A | 10/2007 |
| JP | 2010-120921 A | 6/2010 |
| WO | 2013/084828 A1 | 6/2013 |

OTHER PUBLICATIONS

Communication dated May 17, 2016, from the Intellectual Property Office in Singapore in counterpart Singapore Patent Application No. 11201507992Y.
International Preliminary Report on Patentability dated Sep. 29, 2015 with Written Opinion from the International Bureau in counterpart International Application No. PCT/JP2014/058707.
Extended European Search Report issued Sep. 21, 2016 in counterpart European Patent Application No. 14775559.9.
Notice of Reasons for Rejection issued Sep. 27, 2016 in counterpart Japanese Patent Application No. 2013-063491 with partial English translation.
Communication dated Jul. 19, 2016 from the State Intellectual Property Office of the P.R.C. in counterpart application No. 201480029648.X.
Communication dated Dec. 21, 2016 from the Intellectual Property Office of Singapore in counterpart application No. 11201507992Y.
Chinese Office Action in Application No. 201480029648.X, Apr. 14, 2017.

* cited by examiner

*Primary Examiner* — Yong Chu
*Assistant Examiner* — Ana Z Muresan
(74) *Attorney, Agent, or Firm* — Sughrue Mion, PLLC

(57) ABSTRACT

Production of methacrylic acid ester comprising a step of having acetone undergo a dehydration reaction in the presence of a dehydration reaction catalyst to obtain a reaction mixture; a step of separating a mixture containing propyne and propadiene as main components from the obtained reaction mixture; a step of separating the separated mixture containing propyne and propadiene as main components into a liquid, gas, or gas-liquid mixture containing propyne as a main component, and a liquid, gas, or gas-liquid mixture containing propadiene as a main component; and a step of bringing the obtained liquid, gas, or gas-liquid mixture containing propyne as a main component into contact with carbon monoxide and an alcohol having 1 to 3 carbon atoms in the presence of a catalyst containing at least one selected from the group consisting of Group 8 metal elements, Group 9 metal elements, and Group 10 metal elements.

6 Claims, 3 Drawing Sheets

Heat insulation-type fixed bed

Multi-tubular fixed bed reactor (Reformer type)

Simulated moving bed

Moving bed system

Fluidized bed

METHOD FOR PRODUCING METHACRYLIC ACID ESTER

CROSS REFERENCE TO RELATED APPLICATIONS

This application is a National Stage of International Application No. PCT/JP2014/058707 filed Mar. 19, 2014, claiming priority based on Japanese Patent Application No. 2013-063491, filed Mar. 26, 2013, the contents of all of which are incorporated herein by reference in their entirety.

TECHNICAL FIELD

The present invention relates to a method for producing a methacrylic acid ester.

BACKGROUND ART

JP 2007-269707 A, for example, describes, as a method for producing a methacrylic acid ester, a method comprising thermally decomposing a hydrocarbon selected from propane, propylene, butane, 1-butene, 2-butene, isobutane, isobutene, and butadiene to obtain a decomposed gas in which the total content of propyne and propadiene is 2% by weight or more; subjecting a mixed gas of the decomposed gas thus obtained and a decomposed gas evolving from a plant for thermally decomposing a hydrocarbon having 2 to 10 carbon atoms (common name: ethylene plant) to a separation step shared with the ethylene plant to thereby separate into a mixed solution rich in propyne and propadiene; subjecting the separated mixed solution to extractive distillation to thereby separate into purified propyne and crude propadiene containing propadiene as a main component; and then reacting the thus obtained purified propyne with carbon monoxide and methanol in the presence of a palladium catalyst to thereby produce methyl methacrylate.

Problems to be Solved by the Invention

However, the above-mentioned conventional method had a problem that the resulting methacrylic acid ester is not necessarily satisfactory in view of productivity because of low selectivity to propyne and propadiene obtained by thermal decomposition of a hydrocarbon, and that there is a need to adjacent to an ethylene plant since the method is likely to receive location restrictions, so that there has been required to develop a novel method for producing a methacrylic acid ester, which is less likely to receive location restrictions, and is also economically and industrially advantageous.

Thus, an object of the present invention is to provide a method for producing a methacrylic acid ester, which is less likely to receive location restrictions and is also economically and industrially advantageous.

Means for Solving the Problems

In light of these circumstances, the present inventors have intensively studied, and thus the present invention has been completed. That is, the present invention includes the following configurations.

(1) A method for producing a methacrylic acid ester, which comprises the following steps:

a dehydration reaction step: a step of having acetone undergo a dehydration reaction in the presence of a dehydration reaction catalyst to obtain a reaction mixture containing propyne, propadiene, and water;

a propyne/propadiene separation step: a step of separating a mixture containing propyne and propadiene as main components from the reaction mixture obtained in the dehydration reaction step;

a propyne purification step: a step of separating the mixture containing propyne and propadiene as main components separated in the propyne/propadiene separation step into a liquid, gas, or gas-liquid mixture containing propyne as a main component, and a liquid, gas, or gas-liquid mixture containing propadiene as a main component; and a carbonylation reaction step: a step of bringing the liquid, gas, or gas-liquid mixture containing propyne as a main component obtained in the propyne purification step into contact with carbon monoxide and an alcohol having 1 to 3 carbon atoms in the presence of a catalyst containing at least one selected from the group consisting of Group 8 metal elements, Group 9 metal elements, and Group 10 metal elements to obtain a methacrylic acid ester.

(2) The method according to the above (1), wherein the dehydration reaction catalyst is a catalyst containing silicon and at least one selected from the group consisting of Group 1 metal elements and Group 2 metal elements.

(3) The method according to the above (1) or (2), wherein the reaction mixture in the dehydration reaction step further contains unreacted acetone, and in the propyne/propadiene separation step, a mixture containing the unreacted acetone is obtained by separating the mixture containing propyne and propadiene as main components.

(4) The method according to the above (3), further comprising the following step:

an acetone circulation step: a step of supplying at least a part of acetone contained in the mixture containing the unreacted acetone obtained in the propyne/propadiene separation step to the dehydration reaction step.

(5) The method according to any one of the above (1) to (4), further comprising the following step:

an isomerization reaction step: a step of isomerizing the liquid, gas, or gas-liquid mixture containing propadiene as a main component obtained in the propyne purification step in the presence of an isomerization catalyst to obtain a mixture containing propyne and propadiene as main components.

(6) The method according to any one of the above (1) to (5), further comprising the following step:

a methacrylic acid ester purification step: a step of recovering propyne and an alcohol having 1 to 3 carbon atoms from the reaction mixture containing the methacrylic acid ester obtained in the carbonylation reaction step, the unreacted propyne, and the unreacted alcohol having 1 to 3 carbon atoms, and also purifying the methacrylic acid ester.

(7) The method according to the above (6), further comprising the following step:

an alcohol circulation step: a step of supplying at least a part of the alcohol having 1 to 3 carbon atoms obtained in the methacrylic acid ester purification step to the carbonylation reaction step.

Effects of the Invention

According to the present invention, it is possible to provide a method for producing a methacrylic acid ester, which is less likely to receive location restrictions and is also economically and industrially advantageous.

MODE FOR CARRYING OUT THE INVENTION

Figure 1:
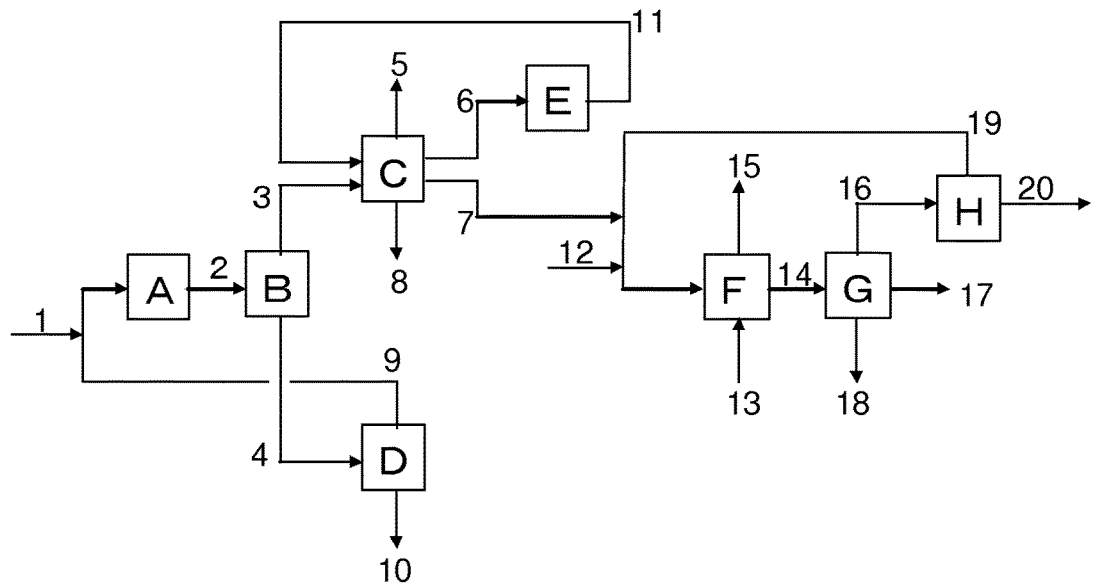
FIG. 1 is an example of a flow of a case where the present invention is carried out.

The present invention includes the below-mentioned dehydration reaction step, propyne/propadiene separation step, propyne purification step, and carbonylation reaction step.

The dehydration reaction step of the present invention is a step of having acetone undergo a dehydration reaction in the presence of a dehydration reaction catalyst to obtain a reaction mixture containing propyne, propadiene, and water. When using acetone, which is a general purpose solvent, as a starting material, it is possible to efficiently obtain propyne, which is a starting material for the production of a methacrylic acid ester, without easily receiving location restrictions.

The dehydration reaction catalyst is preferably a catalyst containing silicon and at least one selected from the group consisting of Group 1 metal elements and Group 2 metal elements. Examples of the catalyst include silicates of Group 1 metal elements; silicates of Group 2 metal elements; and a catalyst in which at least one selected from the group consisting of compounds containing Group 1 metal elements, compounds containing Group 2 metal elements, Group 1 metal elements, and Group 2 metal elements [hereinafter sometimes referred to as the metal component] is supported on a carrier containing silica [hereinafter sometimes referred to as the metal component-supported catalyst]; and a catalyst in which at least one selected from the group consisting of silicates of Group 1 metal elements and silicates of Group 2 metal elements is supported on a carrier containing no silica [hereinafter sometimes referred to as the silicate-supported catalyst]. Of these catalysts, the metal component-supported catalyst and the silicate-supported catalyst are preferable in that propyne and propadiene are obtained with high selectivity. In the metal component-supported catalyst, of at least one selected from the group consisting of compounds containing Group 1 metal elements, compounds containing Group 2 metal elements, Group 1 metal elements, and Group 2 metal elements, at least one selected from the group consisting of compounds containing Group 1 metal elements and Group 1 metal elements is preferable, and compounds containing Group 1 metal elements is more preferable in that propyne and propadiene are obtained with high selectivity. In the silicate-supported catalyst, of the at least one selected from the group consisting of silicates of Group 1 metal elements and silicates of Group 2 metal elements, silicates of Group 1 metal elements are preferable in that propyne and propadiene are obtained with high selectivity.

Examples of the silicates of Group 1 metal elements include lithium silicate ($Li_2O \cdot nSiO_2$, n=1 to 4 [molar ratio]), sodium silicate ($Na_2O \cdot nSiO_2$, n=1 to 4 [molar ratio]), potassium silicate ($K_2O \cdot nSiO_2$, n=1 to 4 [molar ratio]), rubidium silicate ($Rb_2O \cdot nSiO_2$, n=1 to 4 [molar ratio]), and cesium silicate ($Cs_2O \cdot nSiO_2$, n=1 to 4 [molar ratio]). Examples of silicates of Group 2 metal elements include magnesium silicate ($MgO \cdot nSiO_2$, n=1 to 4 [molar ratio]), calcium silicate ($CaO \cdot nSiO_2$, n=1 to 4 [molar ratio]), strontium silicate ($SrO \cdot nSiO_2$, n=1 to 4 [molar ratio]), and barium silicate ($BaO \cdot nSiO_2$, n=1 to 4 [molar ratio]).

In the metal component-supported catalyst, examples of compounds containing Group 1 metal elements include lithium compounds, sodium compounds, potassium compounds, rubidium compounds, and cesium compounds. Of these compounds, sodium compounds, potassium compounds, rubidium compounds, and cesium compounds are preferable in that compounds having an acetylene bond and/or diene are obtained with high selectivity. Of these compounds containing Group 1 metal elements, halides of Group 1 metal elements, carbonates of Group 1 metal elements, oxides of Group 1 metal elements, hydroxides of Group 1 metal elements, and silicates of Group 1 metal elements are preferable, and halides of Group 1 metal elements, oxides of Group 1 metal elements, hydroxides of Group 1 metal elements, and silicates of Group 1 metal elements are more preferable. Of these halides of Group 1 metal elements, chlorides of Group 1 metal elements are preferable.

Examples of the lithium compounds include lithium halides such as lithium fluoride (LiF), lithium chloride (LiCl), lithium bromide (LiBr), and lithium iodide (LiI); oxo acid salts such as lithium carbonate ($Li_2CO_3$), lithium hydrogen carbonate ($LiHCO_3$), lithium sulfate ($Li_2SO_4$), lithium hydrogen sulfate ($LiHSO_4$), lithium sulfite ($Li_2SO_3$), lithium hydrogen sulfite ($LiHSO_3$), lithium nitrate ($LiNO_3$), lithium nitrite ($LiNO_2$), lithium thiosulfate ($Li_2S_2O_3$), lithium silicate ($Li_2O \cdot nSiO_2$, n=1 to 4 [molar ratio]), trilithium phosphate ($Li_3PO_4$), trilithium borate ($Li_3BO_3$), lithium hypochlorite (LiClO), lithium chlorite ($LiClO_2$), lithium chlorate ($LiClO_3$), and lithium perchlorate ($LiClO_4$); oxides and hydroxides, such as lithium oxide ($Li_2O$), lithium peroxide ($Li_2O_2$), and lithium hydroxide (LiOH); organic acid salts such as lithium acetate ($CH_3COOLi$) and lithium citrate; lithium hydride (LiH), lithium sulfide ($Li_2S$), hydrogen sulfide lithium (lithium hydrosulfide) (LiHS), and lithium borohydride ($LiBH_4$). If hydrates thereof exist, hydrates can also be used. If necessary, two or more hydrates thereof may also be used.

Examples of the sodium compounds include sodium halides such as sodium fluoride (NaF), sodium chloride (NaCl), sodium bromide (NaBr), and sodium iodide (NaI); oxo acid salts such as sodium carbonate ($Na_2CO_3$), sodium hydrogen carbonate ($NaHCO_3$), sodium sulfate ($Na_2SO_4$), sodium hydrogen sulfate ($NaHSO_4$), sodium sulfite ($Na_2SO_3$), sodium hydrogen sulfite ($NaHSO_3$), sodium nitrate ($NaNO_3$), sodium nitrite ($NaNO_2$), sodium thiosulfate ($Na_2S_2O_3$), sodium silicate ($Na_2O \cdot nSiO_2$, n=1 to 4 [molar ratio]), trisodium phosphate ($Na_3PO_4$), trisodium borate ($Na_3BO_3$), sodium hypochlorite (NaClO), sodium chlorite ($NaClO_2$), sodium chlorate ($NaClO_3$), and sodium perchlorate ($NaClO_4$); oxides and hydroxides, such as sodium oxide ($Na_2O$), sodium peroxide ($Na_2O_2$), and sodium hydroxide (NaOH); organic acid salts such as sodium acetate ($CH_3COONa$) and sodium citrate; sodium hydride (NaH), sodium sulfide ($Na_2S$), sodium hydrogen sulfide (sodium hydrosulfide) (NaHS), and sodium borohydride ($NaBH_4$). If hydrates thereof exist, hydrates can also be used. If necessary, two or more hydrates thereof may also be used.

Examples of the potassium compounds include potassium halides such as potassium fluoride (KF), potassium chloride (KCl), potassium bromide (KBr), and potassium iodide (KI); oxo acid salts such as potassium carbonate ($K_2CO_3$), potassium hydrogen carbonate ($KHCO_3$), potassium sulfate ($K_2SO_4$), potassium hydrogen sulfate ($KHSO_4$), potassium sulfite ($K_2SO_3$), potassium hydrogen sulfite ($KHSO_3$), potassium nitrate ($KNO_3$), potassium nitrite ($KNO_2$), potassium thiosulfate ($K_2S_2O_3$), potassium silicate ($K_2O.nSiO_2$, n=1 to 4 [molar ratio]), tripotassium phosphate ($K_3PO_4$), potassium borate ($K_3BO_3$), potassium hypochlorite (KClO), potassium chlorite ($KClO_2$), potassium chlorate ($KClO_3$), and potassium perchlorate ($KClO_4$); oxides and hydroxides, such as potassium oxide ($K_2O$), potassium peroxide ($K_2O_2$), and potassium hydroxide (KOH); organic acid salts such as potassium acetate ($CH_3COOK$) and potassium citrate; potassium hydride (KH), potassium sulfide ($K_2S$), potassium hydrogen sulfide (potassium hydrosulfide) (KHS), and potassium borohydride ($KBH_4$). If hydrates thereof exist, hydrates can also be used. If necessary, two or more hydrates thereof may also be used.

Examples of the rubidium compounds include rubidium halides such as rubidium fluoride (RbF), rubidium chloride (RbCl), rubidium bromide (RbBr), and rubidium iodide (RbI); oxo acid salts such as rubidium carbonate ($Rb_2CO_3$), rubidium hydrogen carbonate ($RbHCO_3$), rubidium sulfate ($Rb_2SO_4$), rubidium hydrogen sulfate ($RbHSO_4$), rubidium sulfite ($Rb_2SO_3$), rubidium hydrogen sulfite ($RbHSO_3$), rubidium nitrate ($RbNO_3$), rubidium nitrite ($RbNO_2$), rubidium thiosulfate ($Rb_2S_2O_3$), rubidium silicate ($Rb_2O.nSiO_2$, n=1 to 4 [molar ratio]), trirubidium phosphate ($Rb_3PO_4$), rubidium borate ($Rb_3BO_3$), rubidium hypochlorite (RbClO), rubidium chlorite ($RbClO_2$), rubidium chlorate ($RbClO_3$), and rubidium perchlorate ($RbClO_4$); oxides and hydroxides, such as rubidium oxide ($Rb_2O$), rubidium peroxide ($Rb_2O_2$), and rubidium hydroxide (RbOH); organic acid salts such as rubidium acetate ($CH_3COORb$) and rubidium citrate; rubidium hydride (RbH), rubidium sulfide ($Rb_2S$), rubidium hydrogen sulfide (hydrosulfide rubidium) (RbHS), and rubidium borohydride ($RbBH_4$). If hydrates thereof exist, hydrates can also be used. If necessary, two or more hydrates thereof may also be used.

Examples of the cesium compounds include cesium halides such as cesium fluoride (CsF), cesium chloride (CsCl), cesium bromide (CsBr), and cesium iodide (CsI); oxo acid salts such as cesium carbonate ($Cs_2CO_3$), cesium hydrogen carbonate ($CsHCO_3$), cesium sulfate ($Cs_2SO_4$), cesium hydrogen sulfate ($CsHSO_4$), cesium sulfite ($Cs_2SO_3$), cesium hydrogen sulfite ($CsHSO_3$), cesium nitrate ($CsNO_3$), cesium nitrite ($CsNO_2$), cesium thiosulfate ($Cs_2S_2O_3$), cesium silicate ($Cs_2O.nSiO_2$, n=1 to 4 [molar ratio]), tricesium phosphate ($Cs_3PO_4$), cesium borate ($Cs_3BO_3$), cesium hypochlorite (CsClO), cesium chlorite ($CsClO_2$), cesium chlorate ($CsClO_3$), and cesium perchlorate ($CsClO_4$); oxide and hydroxides, such as cesium oxide ($Cs_2O$), cesium peroxide ($Cs_2O_2$), and cesium hydroxide (CsOH); organic acid salts such as cesium acetate ($CH_3COOCs$) and cesium citrate; cesium hydride (CsH), cesium sulfide ($Cs_2S$), cesium hydrogen sulfide (cesium hydrosulfide) (CsHS), and cesium borohydride ($CsBH_4$). If hydrates thereof exist, hydrates can also be used. If necessary, two or more hydrates thereof may also be used.

Examples of the compounds containing Group 2 metal elements include magnesium compounds, calcium compounds, strontium compounds, and barium compounds. Of these compounds, barium compounds are preferable.

Examples of the magnesium compounds include magnesium halides such as magnesium fluoride ($MgF_2$), magnesium chloride ($MgCl_2$), magnesium bromide ($MgBr_2$), and magnesium iodide ($MgI_2$); oxo acid salts such as magnesium carbonate ($MgCO_3$), magnesium sulfate ($MgSO_4$), magnesium sulfite ($MgSO_3$), magnesium nitrate ($Mg(NO_3)_2$), magnesium nitrite ($Mg(NO_2)_2$), magnesium thiosulfate ($MgS_2O_3$), magnesium silicate ($MgO.nSiO_2$, n=1 to 4 [molar ratio]), magnesium phosphate ($MgHPO_4$), and magnesium borate ($MgB_2O_4$); oxides and hydroxides, such as magnesium oxide (MgO), magnesium peroxide ($MgO_2$), and magnesium hydroxide ($Mg(OH)_2$); organic acid salts such as magnesium acetate ($Mg(CH_3COO)_2$) and magnesium citrate; magnesium hydride ($MgH_2$), and magnesium sulfide (MgS). If hydrates thereof exist, hydrates can also be used. If necessary, two or more hydrates thereof may also be used.

Examples of the calcium compounds include calcium halides such as calcium fluoride ($CaF_2$), calcium chloride ($CaCl_2$), calcium bromide ($CaBr_2$), and calcium iodide ($CaI_2$); oxo acid salts such as calcium carbonate ($CaCO_3$), calcium sulfate ($CaSO_4$), calcium sulfite ($CaSO_3$), calcium nitrate ($Ca(NO_3)_2$), calcium nitrite ($Ca(NO_2)_2$), calcium tiosulfate ($CaS_2O_3$), calcium silicate ($CaO.nSiO_2$, n=1 to 4 [molar ratio]), calcium phosphate ($CaHPO_4$), and calcium borate ($CaB_2O_4$); oxides and hydroxides, such as calcium oxide (CaO), calcium peroxide ($CaO_2$), and calcium hydroxide ($Ca(OH)_2$); organic acid salts, such as calcium acetate ($Ca(CH_3COO)_2$) and calcium citrate; calcium hydride ($CaH_2$), and calcium sulfide (CaS). If hydrates thereof exist, hydrates can also be used. If necessary, two or more hydrates thereof may also be used.

Examples of the strontium compounds include strontium halides such as strontium fluoride ($SrF_2$), strontium chloride ($SrCl_2$), strontium bromide ($SrBr_2$), and strontium iodide ($SrI_2$); oxo acid salts such as strontium carbonate ($SrCO_3$), strontium sulfate ($SrSO_4$), strontium sulfite ($SrSO_3$), strontium nitrate ($Sr(NO_3)_2$), strontium nitrite ($Sr(NO_2)_2$), strontium thiosulfate ($SrS_2O_3$), strontium silicate ($SrO.nSiO_2$, n=1 to 4 [molar ratio]), strontium phosphate ($SrHPO_4$), and strontium borate ($SrB_2O_4$); oxides and hydroxides, such as strontium oxide (SrO), strontium peroxide ($SrO_2$), and strontium hydroxide ($Sr(OH)_2$); organic acid salts such as strontium acetate ($Sr(CH_3COO)_2$) and strontium citrate; strontium hydride ($SrH_2$), and strontium sulfide (SrS). If hydrates thereof exist, hydrates can also be used. If necessary, two or more hydrates thereof may also be used.

Examples of the barium compounds include barium halides such as barium fluoride ($BaF_2$), barium chloride ($BaCl_2$), barium bromide ($BaBr_2$), and barium iodide ($BaI_2$); oxo acid salts such as barium carbonate ($BaCO_3$), barium sulfate ($BaSO_4$), barium sulfite ($BaSO_3$), barium nitrate ($Ba(NO_3)_2$), barium nitrite ($Ba(NO_2)_2$), barium thiosulfate ($BaS_2O_3$), barium silicate ($BaO.nSiO_2$, n=1 to 4 [molar ratio]), barium phosphate ($BaHPO_4$), and barium borate ($BaB_2O_4$); oxides and hydroxides, such as barium oxide (BaO), barium peroxide ($BaO_2$) and barium hydroxide ($Ba(OH)_2$); organic acid salts such as barium acetate ($Ba(CH_3COO)_2$) and barium citrate; barium hydride ($BaH_2$), and barium sulfide (BaS). If hydrates thereof exist, hydrates can also be used. If necessary, two or more hydrates thereof may also be used.

In the metal component-supported catalyst, if Group 1 metal elements are supported, examples of Group 1 metal elements include lithium, sodium, potassium, rubidium, and cesium. Of these elements, sodium, potassium, rubidium, and cesium are preferable. In the metal component-supported catalyst, if Group 2 metal elements are supported, examples of the Group 2 metal elements include magnesium, calcium, strontium, and barium compound. Of these elements, barium is preferable.

In the metal component-supported catalyst, there is no particular limitation on silica source of silica contained in a carrier. For example, it is possible to use a silica powder, a silica sol prepared by using water or an organic solvent as a dispersion medium, an alkoxysilane (tetraethyl orthosilicate, etc.), or the like.

In the metal component-supported catalyst, a carrier containing silica is used. The carrier may contain, in addition to silica, titania, zirconia, and oxides such as niobium oxide and tin oxide. The carrier may be a carrier of silica alone, i.e. a carrier made of silica, or a composite oxide of silica and an oxide except silica, or a mixture of silica and an oxide except silica, and a carrier made of silica is especially preferable.

In the metal component-supported catalyst, examples of the method in which a metal component is supported on a carrier containing silica include an impregnation method, a coprecipitation method, and a kneading method. The metal component-supported catalyst can be prepared, for example, by supporting a metal component on a carrier by an impregnation method, a coprecipitation method, or a kneading method, followed by a heat treatment at 50° C. to 1,000° C. It is also possible to use the supported metal component as a supported oxide after oxidation. It is also possible to use the supported metal component as a supported metal catalyst after reduction. Oxidation is performed by supporting a metal component on a carrier, followed by calcination in an atmosphere of an oxidative gas. The oxidative gas is a gas containing an oxidative substance, and examples thereof include an oxygen-containing gas. The oxygen concentration is usually about 1 to 30% by volume. Air or pure oxygen is usually used as the oxygen source and diluted with an inert gas, if necessary. Of these oxidative gases, air is preferable. The calcination temperature in the oxidation is usually 100 to 1,000° C., and preferably 200 to 800° C. Reduction is performed, for example, by supporting a metal component on a carrier, followed by calcination in an atmosphere of a reducing gas. The reducing gas is a gas containing a reducing substance, and examples thereof include a hydrogen-containing gas, a carbon monoxide-containing gas, and a hydrocarbon-containing gas. The concentration of hydrogen, carbon monoxide, or hydrocarbon is usually about 1 to 30% by volume and the concentration is adjusted, for example, by an inert gas or steam. Of these reducing gases, a hydrogen-containing gas and a carbon monoxide-containing gas are preferable. The calcination temperature in the reduction is usually 100 to 1,000° C., and preferably 200 to 800° C.

The supporting amount of the metal component in the metal component-supported catalyst is preferably 0.01 to 30% by weight, more preferably 0.1 to 20% by weight, and still more preferably 0.1 to 15% by weight, in terms of the weight of a metal element, based on the total amount of the catalyst. If two or more metal elements are contained in the metal component-supported catalyst, the total content of the metal element may fall within the above range.

In the silicate-supported catalyst, examples of silicates of Group 1 metal elements and silicates of Group 2 metal elements include those mentioned above. Examples of the carrier containing no silica include alumina, zirconia, titania, niobium oxide, tin oxide, cerium oxide, lanthanum oxide, magnesium oxide, calcium oxide, neodymium oxide, hafnium oxide, tungsten oxide, silicon carbide, silicon nitride, and activated carbon, and the carrier containing no silica may be a composite oxide containing, as components, two or more components selected from the group consisting of a mixture of two or more components and oxides listed above as examples.

In the silicate-supported catalyst, examples of a method of supporting at least one selected from the group consisting of silicates of Group 1 metal elements and silicates of Group 2 metal elements on a carrier except silica include an impregnation method, a coprecipitation method, and a kneading method. The silicate-supported catalyst can be prepared, for example, by supporting at least one selected from the group consisting of silicates of Group 1 metal elements and silicates of Group 2 metal elements on a carrier by an impregnation method, a coprecipitation method, or a kneading method, or the like, followed by a heat treatment at 50° C. to 1,000° C. After supporting at least one selected from the group consisting of silicates of Group 1 metal elements and silicates of Group 2 metal elements on a carrier, the carrier may be calcined in an atmosphere of an oxidative gas or an atmosphere of a reducing gas. The oxidative gas is a gas containing an oxidative substance, and examples thereof include an oxygen-containing gas. The oxygen concentration is usually about 1 to 30% by volume. Air or pure oxygen is usually used as the oxygen source, and is diluted with an inert gas, if necessary. Of these oxidative gases, air is preferably. The calcination temperature in an atmosphere of the oxidative gas is usually 100 to 1,000° C., and preferably 200 to 800° C. The reducing gas is a gas containing a reducing substance, and examples thereof include a hydrogen-containing gas, a carbon monoxide-containing gas, a hydrocarbon-containing gas, and the like. The concentration of the hydrogen, carbon monoxide, or hydrocarbon is usually about 1 to 30% by volume and concentration is adjusted, for example, by an inert gas or steam. Of these reducing gases, a hydrogen-containing gas and a carbon monoxide-containing gas are preferable. The calcination temperature in an atmosphere of the reducing gas is usually 100 to 1,000° C., and preferably 200 to 800° C.

The supporting amount of at least one selected from the group consisting of silicates of Group 1 metal elements and silicates of Group 2 metal elements in the silicate-supported catalyst is preferably 0.01 to 30% by weight, more preferably 0.1 to 20% by weight, and still more preferably 0.1 to 15% by weight, in terms of the weight of at least one selected from the group consisting of silicates of Group 1 metal elements and silicates of Group 2 metal elements, based on the total amount of the catalyst. In the silicate-supported catalyst, if silicates of Group 1 metal elements and silicates of Group 2 metal elements are contained, the total content may fall within the above range.

A BET specific surface area of the metal component-supported catalyst or silicate-supported catalyst is preferably 1 to 800 $m^2/g$, and more preferably 1 to 400 $m^2/g$. The BET specific surface area of more than 800 $m^2/g$ may lead to deterioration of heat stability of the catalyst. In the metal component-supported catalyst or silicate-supported catalyst, the BET specific surface area of less than 1 $m^2/g$ may lead to deterioration of dispersibility of the supported metal component. Here, the BET specific surface area is the value obtained by measuring using a specific surface area analyzer utilizing a nitrogen adsorption method as the principle.

A pore volume of the metal component-supported catalyst or silicate-supported catalyst is preferably 0.05 to 2.5 ml/g, and more preferably 0.1 to 1.5 ml/g. The pore volume of less than 0.05 ml/g may lead to a decrease in pore diameter, thus causing low activity. Whereas, the pore volume of more than 2.5 ml/g may leads to a reduction in mechanical strength of the catalyst, so that the catalyst is likely to deteriorate. The pore volume is the value obtained by measuring using a mercury penetration method.

The dehydration reaction catalyst is preferably used as a molded body. Examples of the shape include a spherical granular shape, a columnar shape, a pellet shape, an extrusion shape, a ring shape, a honeycomb shape, or a granular shape having an appropriate size obtained by pulverization and screening after molding. The shape of the molded body is selected in accordance with the reaction system to be used. For example, when the molded body is used as the catalyst of the fixed bed reaction, the above-mentioned molded bodies having various shapes are used. In this case, the diameter of the molded body is preferably 10 mm or less. Too large diameter of the molded body may sometimes lead to a decrease in conversion rate of the dehydration reaction. There is no particular limitation on the lower limit of the diameter of the molded body. Too small diameter may lead to large pressure loss in a catalyst layer, so that a molded body having a diameter of 0.5 mm or more is usually used. When the molded body is used as the catalyst of a fluidized bed reaction or a moving bed reaction, a spherical granular molded body having an average particle diameter of about 1 to 1,000 μm is preferably used. Particularly in the fluidized bed reaction, a spherical granular molded body having an average particle diameter of 10 to 500 μm is preferably used. The diameter of the molded body as used herein means a diameter of a sphere for a spherical granular shape, a diameter of a circular cross-section for a columnar shape, or a maximum diameter of a cross-section for other shapes.

In the dehydration reaction, steam, carbon monoxide, carbon dioxide, methane, ethane, ethylene, acetylene, propane, propylene, propyne, propadiene, butane, butene, butyne, isobutylene, butadiene, nitrogen, and the like may exist in the reaction system, together with acetone which is a starting material.

In the dehydration reaction, the reaction temperature is usually 200 to 1,200° C., preferably 250 to 1,000° C., and more preferably 400 to 800° C. The reaction temperature of lower than 200° C. may lead to proceeding of a dehydration reaction with difficulty in view of the reaction rate and chemical equilibrium. Whereas, the reaction temperature of higher than 1,200° C. may lead to deterioration of activity of the catalyst.

In the dehydration reaction, the reaction pressure is usually 0.001 to 5 MPa, and preferably 0.005 to 0.3 MPa. The reaction pressure of lower than 0.001 MPa may lead to deterioration of productivity, whereas, the reaction pressure of higher than 5 MPa may lead to a decrease in conversion rate of acetone due to restriction of chemical equilibrium in the reaction.

When the dehydration reaction is performed in a continuous manner, the supply rate of a starting material gas containing acetone is 1 to 20,000 h$^{-1}$, and preferably 10 to 10,000 h$^{-1}$, per 1 L of the catalyst starting material gas supply rate (L/h; in terms of 0° C., 0.1 MPa), that is, in terms of a gas hourly space velocity (GHSV). The concentration of acetone in the starting material gas containing acetone is appropriately set taking productivity and catalytic activity into consideration. The acetone concentration in the starting material gas may be adjusted by using an inert gas such as nitrogen, methane, ethane, propane, carbon dioxide, and steam in the dehydration reaction.

The dehydration reaction can be carried out by various reaction systems such as a fixed bed system, a simulated moving bed system, a fluidized bed system, and a moving bed system, and a fixed bed system, a simulated moving bed system, or a fluidized bed system is preferable. A dehydration reaction catalyst may be used alone, or may be used after substantially diluting with or mixed with an inert substance. When the dehydration reaction is performed by the fixed bed system, it is possible to use, as the fixed bed reactor to be used, various flow fixed bed reactors in which the reactor is provided with a starting material supply port and a reaction mixture takeout port. There is no particular limitation on the number of reaction tubes, and both monotubular fixed bed reactors and multi-tubular fixed bed reactors can be used. It is also possible to use a heat insulation-type or heat-exchange type fixed bed reactor. When the dehydration reaction is carried out by the fixed bed system using a multi-tubular fixed bed reactor, the dehydration reaction can be carried out, for example, by the method disclosed in EP 1016641 A, etc. When the dehydration reaction is carried out by the simulated moving bed system, the dehydration reaction can be carried out, for example, by the methods disclosed in GB 794089 A, U.S. Pat. Nos. 5,510,557, 5,315,056, WO 95/23123 A, etc. When the dehydration reaction is carried out by the moving bed system, the dehydration reaction can be carried out, for example, by the methods disclosed in U.S. Pat. Nos. 5,321,192, 5,227,567, 5,177,293, etc. When the dehydration reaction is carried out by the fluidized bed system, the dehydration reaction can be carried out, for example, by the method disclosed in U.S. Pat. No. 6,362,385.

The dehydration reaction is a reaction with significant heat absorption of 161 kJ/mol and there is a need to supply reaction het so as to continuously continue the reaction. In the case of performing the reaction, it is preferred to use a reactor provided with an equipment capable of supplying reaction heat. If the dehydration reaction is performed, as the reaction time advances, in other words, as the total throughput per unit weight of the catalyst of acetone increases, so-called coke (carbon component) gradually adheres to the dehydration reaction catalyst due to fusion or polymerization of acetone, propyne, propadiene and/or by-products, so that catalytic activity gradually deteriorates, that is, the conversion rate of acetone gradually decreases. Therefore, in the production method of the present invention, it is preferred to provide a dehydration reaction catalyst regeneration step of performing a heat treatment in an atmosphere of an oxygen-containing gas so as to recover catalytic activity in the dehydration reaction by removing coke from the dehydration reaction catalyst with coke adhered thereon.

A detailed description will be made for an example of a case where a dehydration reaction step is carried out by a fixed bed system using a heat insulation-type fixed bed reactor in the present invention with reference to FIG. 2.

Figure 2:
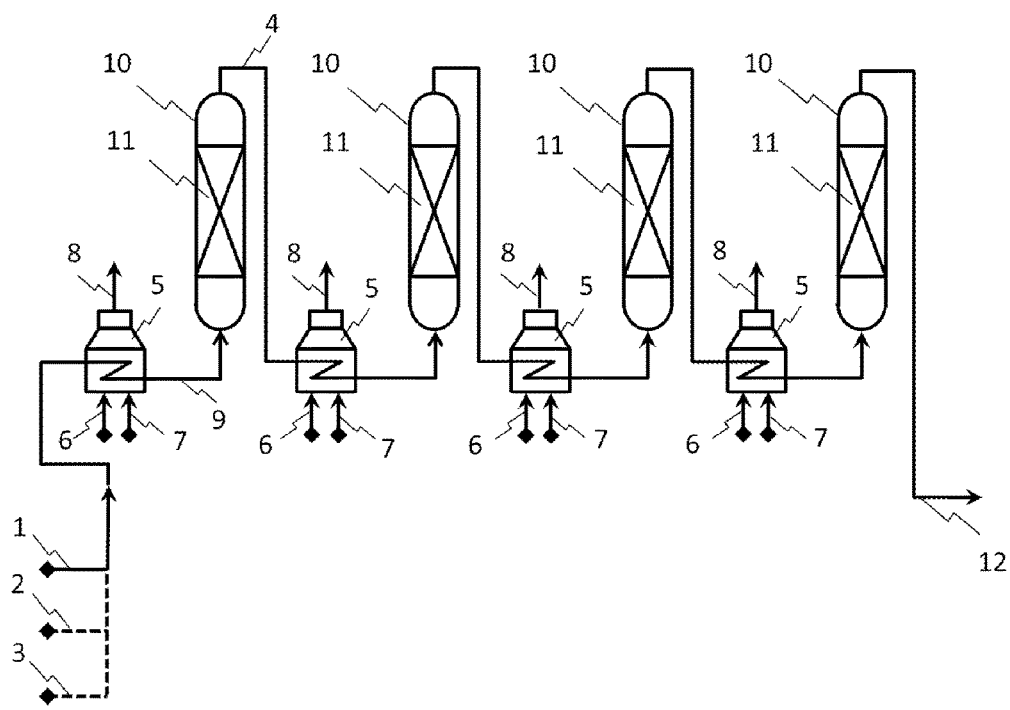
FIG. 2 is a schematic view showing an example of a case where a dehydration reaction step is carried out by a fixed bed system using a heat insulation-type fixed bed reactor in the present invention.

In FIG. 2, a starting material containing acetone to be supplied through a starting material supply line 1 is preheated in a preheater 5, passed through a preheated starting material gas supply line 9 after being preheated, and supplied to a heat insulation-type fixed bed reactor 10 having a solid catalyst layer 11 packed with a dehydration reaction catalyst. In that case, the starting material is supplied after preheating to the temperature higher than the reaction temperature by the preheater 5 to thereby allow the reaction to proceed. Reaction heat is supplied by this preheating. There is no particular limitation on preheater 5, and it is preferred to use a heating furnace using, as a heat source, a combustion gas to be supplied through a combustion gas supply line 6 and/or combustion air to be supplied through a combustion air supply line 7. The combustion gas and/or combustion air is/are heat-exchanged in the preheater 5 and discharged through a preheater waste gas line 8. In the heat insulation-type fixed bed reactor 10, as the reaction proceeds, the temperature falls toward an outlet and also the reaction rate decreases. The reactor outlet gas thus obtained is appropriately cooled in a heat exchanger (not shown) and taken out as a reaction mixture through a reaction mixture takeout line 12.

It is possible to adjust the acetone conversion rate in the heat insulation-type fixed bed reactor 10 by the preheating temperature. The conversion rate can be increased by increasing the preheating temperature, however, if the preheating temperature is too high, an increase in thermal decomposition of acetone by the preheater 5 (heating furnace) leads to a decrease in yield of the target component and also a rise in heating tube surface temperature of the preheater 5 leads to an increase in precipitation (caulking) rate of a carbon component on an inner surface of a tube, which may cause a decrease in heat transfer efficiency within a short time. Therefore, the preheating temperature is desirably 750° C. or lower. It is also possible to suppress a rise in preheating temperature per stage to thereby increase the total acetone conversion rate by using the preheaters 5 and the heat insulation-type fixed bed reactors 10 in combination and arranging them in series via the reacted gas takeout line 4 to form a multi-stage structure. The number of stages to be arranged in series is preferably 2 to 10. FIG. 2 shows an example of four stages.

Differential pressure of the dehydration reaction catalyst to be packed in the heat insulation-type fixed bed reactor 10 is preferably as low as possible. There is no particular limitation on shape, and examples of the shape include a cylinder shape and a spherical shape. The particle equivalent diameter is preferably 2 to 10 mm.

When it became impossible to obtain desired catalytic activity as a result of continuation of the dehydration reaction, supply of the starting material is stopped and an inert gas such as nitrogen or steam is supplied through the inert purge gas line 3 to thereby replace the atmosphere inside the heat insulation-type fixed bed reactor 10 by the inert gas, and then coke precipitated on the catalyst is burnt-off by supplying an oxygen-containing gas through the oxygen-containing gas line 2 at high temperature, thus enabling regeneration of the catalyst. Usually, the flow rate, temperature, oxygen concentration, etc. of the oxygen-containing gas are adjusted so as to control temperature rise of the solid catalyst layer 11 during the regeneration operation. After completion of the regeneration operation, the atmosphere inside the heat insulation-type fixed bed reactor 10 is replaced by an inert gas by supplying the inert gas such as nitrogen or steam through the inert purge gas line 3, and then the reaction is usually restarted by starting supply of the starting material. Alternatively, after discharging the gas inside the heat insulation-type fixed bed reactor 10 by pressure reduction, the reaction is restarted by starting supply of the starting material again. It is also possible to perform removal (decaulking) of coke adhered to a heating tube of the preheater 5 by a similar operation.

A detailed description will be made for an example of a case where a dehydration reaction step is carried out by a fixed bed system using a multi-tubular fixed bed reactor in the present invention with reference to FIG. 3.

Figure 3:
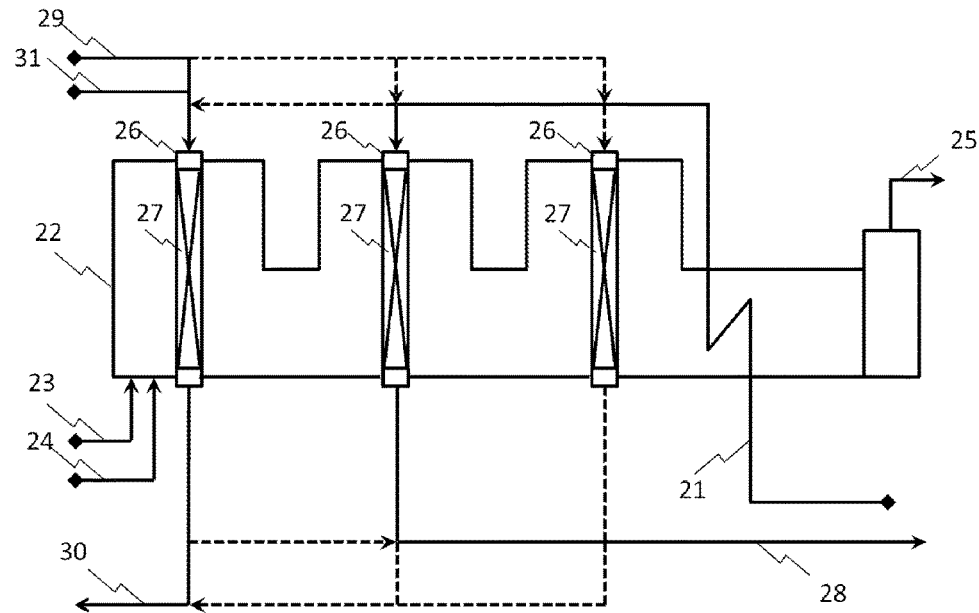
FIG. 3 is a schematic view showing an example of a case where a dehydration reaction step is carried out by a fixed bed system using a multi-tubular fixed bed reactor in the present invention.

In FIG. 3, a starting material containing acetone to be supplied through a starting material supply line 21 is supplied to a plurality of fixed bed reaction tubes 26 having a solid catalyst layer 27 packed with a dehydration reaction catalyst. Using a heating furnace 22, reaction heat is supplied by heating (performing heat exchange) from the outside of the fixed bed reaction tube 26 with a heat source (combustion gas, etc.) having the temperature higher than the reaction temperature. The heating furnace 22 can be used for preheating of a starting material, in addition to heating of the fixed bed reaction tube 26. Regarding the heating furnace 22, a combustion gas to be supplied through a combustion gas supply line 23 and/or combustion air to be supplied through a combustion air supply line 24 is/are usually used as the heat source. The reaction mixture is taken out from an outlet of the fixed bed reaction tube 26 through a reaction mixture takeout line 28, and then sent to the next step.

The acetone conversion rate in the fixed bed reaction tube 26 is controlled by the temperature of the heating furnace 22 outside the fixed bed reaction tube 26. The conversion rate can be increased by increasing the heating furnace 22, however, if the temperature is too high, the temperature of an inner surface of the fixed bed reaction tube 26 rises, leading to an increase in precipitation (caulking) rate of a carbon component on an inner surface of a tube, which may cause a decrease in heat transfer efficiency of the fixed bed reaction tube 26 within a short time. Since the temperature of a solid catalyst layer 27 also becomes high, the caulking rate to a surface of the catalyst may increase, leading to deterioration of catalytic activity within a short period.

When it became impossible to obtain desired catalytic activity as a result of continuation of the dehydration reaction, supply of the starting material is stopped and an inert gas such as nitrogen or steam is supplied through the inert purge gas line 29 to thereby replace the atmosphere inside the fixed bed reaction tube 26 by the inert gas, and then coke precipitated on the catalyst and coke precipitated inside the fixed bed reaction tube 26 are burnt-off by supplying an oxygen-containing gas through an oxygen-containing gas line 31 at high temperature, thus making it possible to regenerate the catalyst and to perform decoking inside the fixed bed reaction tube 26. The gas after being used for burning-off of coke is discharged through a regenerated off-gas line 30. Usually, the flow rate, temperature, oxygen concentration, etc. of the oxygen-containing gas are adjusted so as to control temperature rise of the solid catalyst layer 27 during burning-off operation (regeneration operation) of coke. After completion of the regeneration operation, the atmosphere inside the fixed bed reaction tube 26 is replaced by an inert gas by supplying the inert gas such as nitrogen or steam through the inert purge gas line 29, and then the reaction is usually restarted by starting supply of the starting material. Plural fixed bed reaction tubes 26 are arranged in parallel to thereby switch the reaction and the regeneration operation, thus making it possible to continuously continue the reaction. FIG. 3 shows an example in which three series fixed bed reaction tubes 26 are arranged in parallel.

Usually, the heating furnace 22 is heated by a combustion gas and/or combustion air and heats the fixed bed reaction tube 26 and the starting material, and also heat is recovered as steam at a downstream of the heating furnace by supplying water to a boiler and then discharged through a heating furnace waste gas line 25.

A detailed description will be made for an example of a case where a dehydration reaction step is carried out by a simulated moving bed system in the present invention with reference to FIG. 4.

Figure 4:
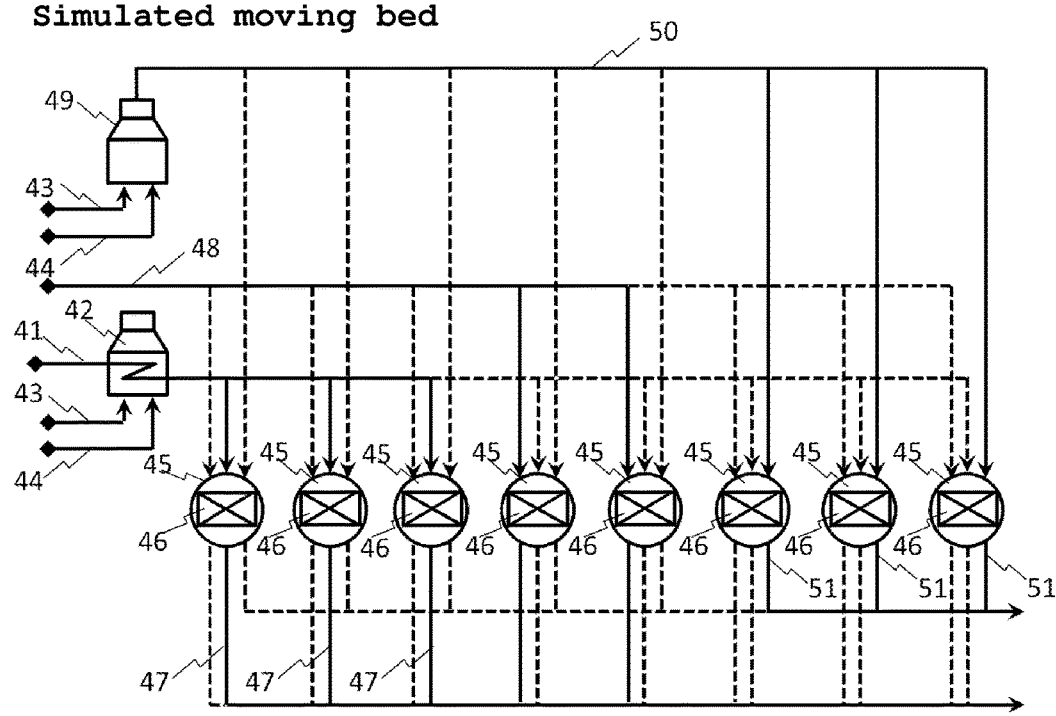
FIG. 4 is a schematic view showing an example of a case where a dehydration reaction step is carried out by a simulated moving bed system in the present invention.

In FIG. 4, when the following steps (i) to (iv) are carried out by each reactor using plural heat insulation-type fixed bed reactors 45 having a solid catalyst layer 46 (usually 3 to 20 reactors) in parallel, while the step (i) is carried out by some reactors, reaction, supply of a reaction heat, and regeneration of the catalyst are carried out in the remaining reactors while switching the reactor by the method of carrying out the steps (ii) to (iv) and the reaction is continuously reacted, whereby, the hydration reaction step can be carried out by the simulated moving bed system:

(i) a reaction step: a step in which a starting material containing acetone to be supplied through a starting material supply line 41 is indirectly heated by a preheater 42 heated by a combustion gas to be supplied through a combustion gas supply line 43 and/or an oxygen-containing gas to be supplied through an oxygen-containing gas line 44, and then is supplied to the heat insulation-type fixed bed reactor 45 having a solid catalyst layer 46 preheated in a predetermined temperature, so that acetone is subjected to a dehydration reaction by contacting with a dehydration reaction catalyst to obtain a reaction mixture through a reaction mixture takeout line 47;

(ii) a combustible gas removing step: a step in which the inside of the heat insulation-type fixed bed reactor 45 is connected to a pressure reducing device to thereby remove combustible gas inside the reactor, or a step in which the inside of heat insulation-type fixed bed reactor 45 is replaced by an inert gas by supplying a gas, which is inert relative to the dehydration reaction and is incombustible, such as nitrogen, carbon dioxide, or steam through an inert purge gas line 48;

(iii) a heating/regeneration step: a step in which a combustion gas and/or an oxygen-containing gas is/are heated to the temperature higher than the reaction temperature in a heating furnace for catalyst regeneration 49, and the catalyst regenerated gas thus obtained is supplied to the heat insulation-type fixed bed reactor 45 through a catalyst regenerated gas supply line 50 to thereby heat the solid catalyst layer 46, and then coke precipitated on a dehydration reaction catalyst is burnt-off to thereby regenerate the catalyst; and (iv) a regenerated gas removing step: a step in which the heat insulation-type fixed bed reactor 45 is connected to a pressure reducing device to thereby remove a catalyst regenerated gas inside, or a step in which the inside of heat insulation-type fixed bed reactor 45 is replaced by an inert gas by supplying a gas, which is inert relative to the dehydration reaction and is incombustible, such as nitrogen, carbon dioxide, or steam through an inert purge gas line 48.

In the above-mentioned step (i), after continuation of the dehydration reaction for a predetermined time until it became impossible to obtain the desired catalytic activity, supply of a starting material is stopped and then the step (ii) is carried out. The reaction time per cycle, up to stoppage of supply of the starting material from starting of supply of the starting material, is preferably about 5 to 30 minutes.

In the above-mentioned step (iii), combustion heat of coke precipitated on the dehydration reaction catalyst also contributes to temperature rise of the solid catalyst layer. The catalyst regenerated gas after being used for burning-off of coke is discharged from an outlet of the heat insulation-type fixed bed reactor 45 through a regenerated off-gas line 51. If necessary, the catalyst regenerated gas heated to high temperature is supplied to the heat insulation-type fixed bed reactor 45 while adjusting the temperature until the solid catalyst layer 46 reaches the predetermined temperature. At the point of time when the solid catalyst layer 46 reaches the predetermined temperature, supply of the catalyst regenerated gas heated to high temperature is stopped and the solid catalyst layer 46 is retained at the predetermined temperature for a predetermined time. The supply rate (kg/h) per hour of the catalyst regenerated gas is preferably 2 to 20 times the supply rate (kg/h) of acetone supplied to the heat insulation-type fixed bed reactor 45 in the step (i). A ventilation direction of the catalyst regenerated gas may be either the same flow direction of the starting material containing acetone in the step (i), or a reverse direction. The regeneration time per cycle is usually 5 to 30 minutes.

Reaction heat required for the above-mentioned reaction step (i) is supplied by a combustion gas and/or an oxygen-containing gas, which is/are supplied in a heating/regeneration step in second cycle or later, and a change in sensible heat corresponding to a difference between the temperature after completion of the reaction step and the temperature after completion of the heating/regeneration step of the solid catalyst layer 46 corresponds to reaction heat required for the reaction step. Therefore, this temperature difference is proportional to the amount of acetone which reacts during 1 cycle of the steps (i) to (iv).

The acetone reaction amount per cycle is adjusted by the heating temperature of the solid catalyst layer 46 by the heating/regeneration step. The temperature of the heating/regeneration step is preferably set at the temperature which is 10 to 50° C. higher than the reaction temperature, and it is desirable to adjust the temperature of the catalyst regenerated gas to be supplied to the heat insulation-type fixed bed reactor 45 so that the temperature of the heating/regeneration step becomes 750° C. or lower. The temperature of the solid catalyst layer 46 can be controlled by the temperature, oxygen concentration, supply flow rate, and ventilation time of the catalyst regenerated gas. If the temperature of the solid catalyst layer 46 in the heating/regeneration step is too high, an increase in thermal decomposition in the reaction step may lead to a decrease in yield and also an increase in coke precipitation rate on a surface of the catalyst may lead to deterioration of catalytic activity within a short period. High concentration of coke precipitated on the dehydration reaction catalyst in the reaction step may cause heat deterioration of the catalyst due to excess temperature rise in the subsequent heating/regeneration step.

Examples of the method in which the acetone reaction amount per cycle is increased while retaining the temperature of the solid catalyst layer 46 after the heating/regeneration step low include a method in which heat capacity of the solid catalyst layer 46 by mixing a dehydration reaction catalyst with a diluted heating medium. The diluted heating medium may be solid particles which are inert for the reaction and are thermally stable, and examples thereof usually include ceramic materials such as alumina, zirconia, titania, zirconia ceramics, silica, quartz, silicon carbide, and silicon nitride; metallic materials such as iron, nickel, titanium, zirconium, and chromium; and stainless steel materials such as SUS316, SUS316L, SUS304, and SUS310S, and preferably ceramic materials such as α-alumina, zirconia ceramics, quartz, and silicon carbide.

In the reaction step, the starting material may be preheated. That is, it is also possible to control the acetone conversion rate in the heat insulation-type fixed bed reactor 45 by the preheating temperature. The reaction rate can be increased by increasing the preheating temperature. If the preheating temperature is too high, an increase in thermal decomposition of acetone by a preheater 42 may lead to a decrease in yield of the target component and also a rise in heating tube surface temperature of the preheater 42 leads to an increase in caulking rate on an inner surface of a tube, which may cause a decrease in heat transfer efficiency within a short time. If coke is precipitated inside the preheater 42, supply of the starting material is stopped and an inert gas such as nitrogen or steam is supplied to thereby replace the atmosphere inside the preheater by the inert gas, and then coke is burnt-off by supplying an oxygen-containing gas at high temperature, followed by heating.

Differential pressure of the dehydration reaction catalyst to be packed in the heat insulation-type fixed bed reactor 45 is preferably as low as possible. There is no particular limitation on shape, and examples thereof include a cylinder shape and a spherical shape. The particle equivalent diameter is preferably 2 to 10 mm.

A detailed description will be made for an example of a case where a dehydration reaction step is carried out by a moving bed system in the present invention with reference to FIG. 5.

Figure 5:
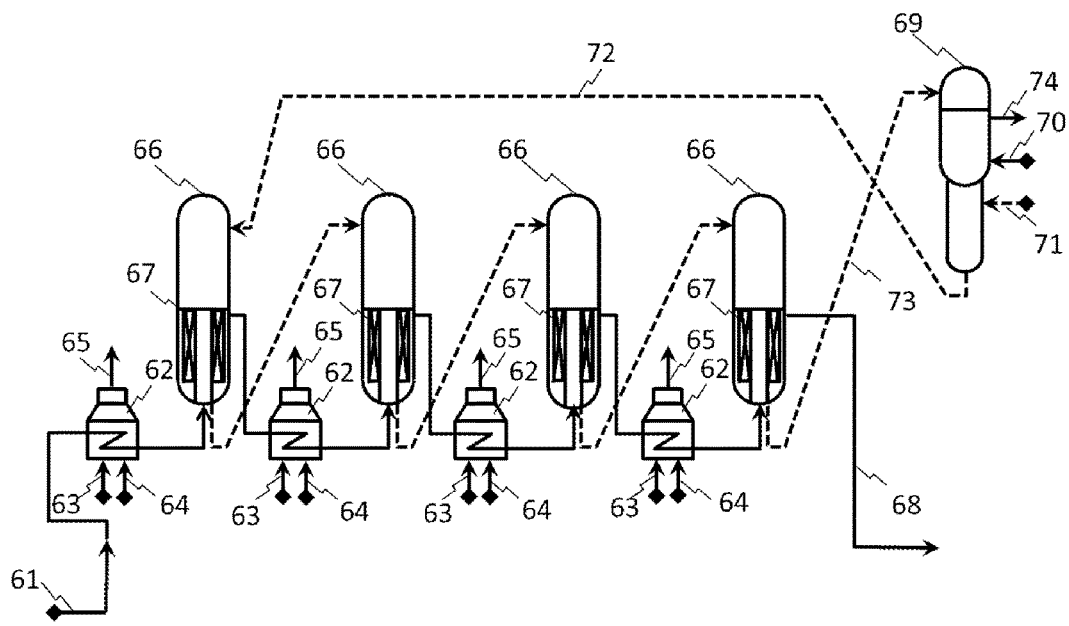
FIG. 5 is a schematic view showing an example of a case where a dehydration reaction step is carried out by a moving bed system in the present invention.

In FIG. 5, the configuration is the same as that in a case where the dehydration reaction step is carried out by the above-mentioned fixed bed system using a heat insulation-type fixed bed reactor, except that the heat insulation-type fixed bed reactor is a heat insulation-type moving bed reactor. That is, a dehydration reaction catalyst is continuously or intermittently supplied from the upper portion of a heat insulation-type moving bed reactor 66, and then brought into contact with a starting material containing acetone, which is supplied through a starting material supply line 61 and preheated in a preheater 62, while moving downward of the catalyst moving layer 67 due to gravity, whereby, the dehydration reaction proceeds to obtain a reaction mixture through a reaction mixture takeout line 68. There is no particular limitation on preheater 62, and it is preferred to use an indirect heating furnace using, as a heat source, a combustion gas to be supplied through a combustion gas supply line 63 and/or combustion air to be supplied through a combustion air supply line 64. The combustion gas and/or combustion air is/are heat-exchanged in the preheater 62 and then discharged through a preheater waste gas line 65. In a heat insulation-type moving bed reactor 66, as the reaction proceeds, the temperature falls toward an outlet and also the reaction rate decreases.

The acetone conversion rate in the heat insulation-type moving bed reactor 66 can be adjusted by the preheating temperature. The acetone conversion rate can be increased by increasing the preheating temperature, however, if the preheating temperature is too high, an increase in thermal decomposition of acetone in the preheater 62 leads to a decrease in yield of the target component and also a rise in heating tube surface temperature of the preheater 62 leads to an increase in caulking rate on an inner surface of a tube, which may cause a decrease in heat transfer efficiency within a short time. Therefore, the preheating temperature is desirably 750° C. or lower. It is also possible to suppress a rise in preheating temperature per stage to thereby increase the total acetone conversion rate by arranging the preheaters 62 and the heat insulation-type moving bed reactors 66 in series to form a multi-stage structure. The number of stages to be arranged in series is preferably 2 to 10. FIG. 5 shows an example of four stages.

A moving direction of the catalyst moving layer 67 and a flow direction of the starting material may be either a co-current flow or counter-current flow direction (FIG. 5 shows an example of a counter-current flow). When the heat insulation-type moving bed reactors 66 are arranged in series to form a multi-stage structure, the catalyst may be circulated between each heat insulation-type moving bed reactor 66 and each catalyst regenerator 69. Alternatively, the system may be a co-current transfer system in which the catalyst is moved toward a downstream reactor from an upstream reactor in a flow direction of a starting material via a used catalyst transfer tube 73, and then the catalyst is transferred to a catalyst reaction column 69 from the downmost-stream reactor. To the contrary, the system may be a counter-current transfer system in which the catalyst is transferred to an upstream reactor from a downmost stream reactor, and then the catalyst is transferred to a regeneration column from an uppermost stream reactor. FIG. 5 shows an example of a co-current transfer system.

Usually, used catalyst with activity deteriorated by adhesion of coke is continuously or intermittently withdrawn from the bottom of the heat insulation-type moving bed reactor 66. The catalyst thus withdrawn is conveyed via a used catalyst transfer tube 73 and then continuously or intermittently supplied to the upper portion of the catalyst regenerator 69. The catalyst is contacted with a heated oxygen-containing gas to be supplied to the catalyst regenerator 69 through the oxygen-containing gas line 70 while moving downward in the catalyst regenerator 69 due to gravity, and then regenerated as a result of burning-off of the precipitated coke. The catalyst thus generated is continuously or intermittently withdrawn from the bottom of the catalyst regenerator 69, conveyed via the regenerated catalyst transfer tube 72, and then continuously or intermittently supplied to the upper portion of the heat insulation-type moving bed reactor 66. The oxygen-containing gas used in the catalyst regenerator 69 is discharged through the regenerated off-gas line 74.

A moving direction of the catalyst layer and a gas in the catalyst regenerator 69 may be either a co-current flow or counter-current flow direction (FIG. 5 shows an example of a counter-current flow). If loss of the generation catalyst occurs, a supplementing catalyst may be added to the catalyst regenerator 69 through a supplementing catalyst supply line 71.

When coke is precipitated inside the preheater 62, supply of the starting material is stopped and an inert gas such as nitrogen or steam is supplied to thereby replace the atmosphere inside the preheater by the inert gas, and then coke is burnt-off by supplying an oxygen-containing gas at high temperature, followed by heating.

A detailed description will be made for an example of a case where a dehydration reaction step is carried out by a fluidized bed system in the present invention with reference to FIG. 6.

Figure 6:
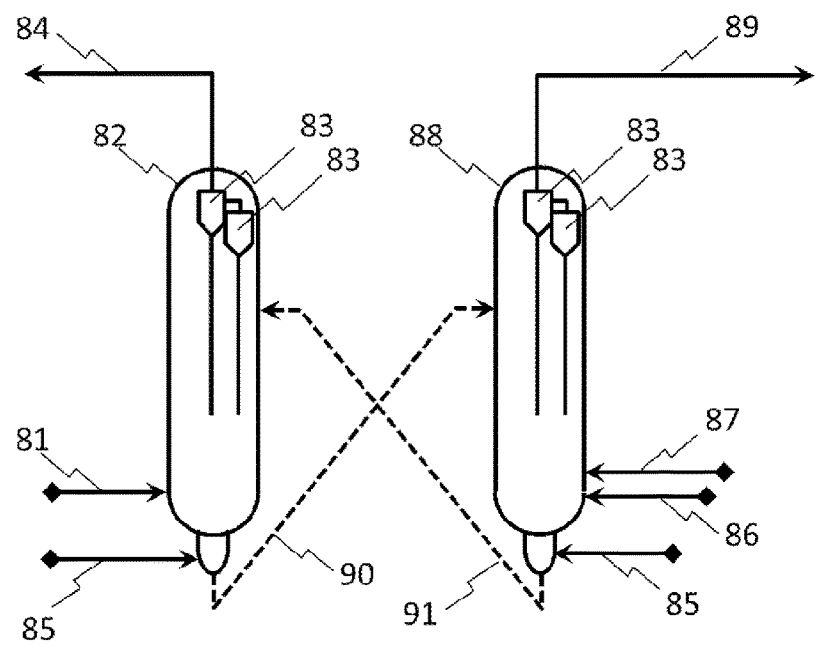
FIG. 6 is a schematic view showing an example of a case where a dehydration reaction step is carried out by a fluidized bed system in the present invention.

In FIG. 6, a dehydration reaction catalyst heated in a reaction column 82 forms a fluidized bed, together with an inert gas such as nitrogen, carbon dioxide, vapor, methane, ethane, or propane to be supplied through a catalyst transfer gas line 85, which is inert relative to the dehydration reaction, and then a starting material containing acetone is supplied through a starting material supply line 81 to thereby allow the dehydration reaction to proceed. The gas obtained after the reaction is taken out as a reaction mixture through a reaction mixture takeout line 84. Required reaction heat is supplied by heat transfer due to contact between the heated dehydration reaction catalyst and the starting material. The reaction column 82 is provided with a cyclone 83 at the upper portion, which causes separation of the dehydration reaction catalyst which entrains the reaction gas and returning of the dehydration reaction catalyst to the reaction column 82.

Since activity of the catalyst which retains in the reaction column 82 deteriorates as coke is precipitated, used catalyst is withdrawn from the reaction column 82 via a used catalyst transfer tube 90. The catalyst thus withdrawn is supplied to a regeneration column 88, together with a gas, which is inert relative to the dehydration reaction and is incombustible, such as nitrogen, carbon dioxide, or steam to be supplied through the catalyst transfer gas line 85, regenerated and then recirculated to the reaction column 82 via a regenerated catalyst transfer tube 91, together with a gas, which is inert relative to the dehydration reaction and is incombustible, such as nitrogen, carbon dioxide, or steam. In the regeneration column 88, used catalyst with coke precipitated thereon is brought into contact with a high-temperature combustion gas to be supplied through a combustion gas supply line 86 and/or a high-temperature oxygen-containing gas to be supplied through an oxygen-containing gas line 87 in a fluidized bed state, whereby, coke is burnt-off to thereby regenerate the catalyst and heat the catalyst by heat transfer from the high-temperature gas. The regeneration column 88 is also provided with a cyclone 83 at the upper portion, which causes separation of the dehydration reaction catalyst from the regeneration column outlet gas and returning of the dehydration reaction catalyst to the regeneration column 88. The regeneration column outlet gas is discharged through a regenerated off-gas line 89.

When the dehydration reaction step is carried out by the fluidized bed system, use of a solid catalyst having a particle size distribution of 10 to 500 μm and a static bulk density of 300 to 2,000 kg/m$^3$ as the dehydration reaction catalyst enables formation of a satisfactory fluidized bed. There is no particular limitation on fluidization regime, and a fast fluidization regime like the Riser section of fluidized catalytic cracking (FCC system) may be formed by setting a gas flow rate at 2 to 20 m/s, or a dense bed may be formed by setting a gas flow rate at 0.1 to 2 m/s.

The dehydration reaction catalyst continuously or intermittently circulates in a reaction column 82 and a regeneration column 88, and the acetone conversion rate in the reaction column 82 can be adjusted by controlling the circulation amount and the temperature in the regeneration column 83. Since too high heating temperature of the dehydration reaction catalyst in the regeneration column 83 leads to heat deterioration of the dehydration reaction catalyst and an increase in thermal decomposition reaction in the reaction column 82, the heating temperature is preferably set at the temperature which is 20 to 50° C. higher than the reaction temperature, and it is desirable to adjust the temperature of the combustion gas and/or oxygen-containing gas to be supplied to the regeneration column 88 so that the heating temperature becomes 750° C. or lower. The catalyst circulation amount (kg/h) per hour of the catalyst circulating in the reaction column 82 and the regeneration column 88 is preferably 3 to 10 times the supply rate (kg/h) of acetone to be supplied through the starting material supply line 81.

The reaction heat required for the dehydration reaction may be supplied by preheating of the starting material using a preheater (not shown), in addition to heating of the above-mentioned dehydration reaction catalyst. That is, the acetone conversion rate in the reaction column 82 can be controlled by the preheating temperature of the starting material, in addition to heating of the catalyst. The acetone conversion rate can be increased by increasing the preheating temperature of the starting material. If the preheating temperature is too high, an increase in thermal decomposition of acetone in a preheater (heating furnace) may lead to a decrease in yield of the target component and also a rise in heating tube surface temperature of a starting material preheating furnace leads to an increase in caulking rate on an inner surface of a tube, which may cause a decrease in heat transfer efficiency within a short time. If coke is precipitated inside the preheater, supply of the starting material is stopped and an inert gas such as nitrogen or steam is supplied to thereby replace the atmosphere inside the preheater by the inert gas, and then coke is burnt-off by supplying an oxygen-containing gas at high temperature, followed by heating.

The propyne/propadiene separation step of the present invention is a step of separating a mixture containing propyne and propadiene as main components from the reaction mixture obtained in the dehydration reaction step.

The reaction mixture obtained in the dehydration reaction step contains reaction products such as propyne, propadiene, and water, and also can contain the unreacted acetone, by-products, and so on. When the reaction mixture obtained in the dehydration reaction step contains the unreacted acetone, it is preferred to obtain a mixture containing the unreacted acetone by separating so that the remaining mixture obtained by separating the mixture containing propyne and propadiene as main components from the reaction mixture contains the unreacted acetone. Water contained in the reaction mixture may be removed by subjecting the reaction mixture to a dehydration treatment before subjecting to separation, or may be contained in the mixture containing propyne and propadiene as main components, or may be contained in the remaining mixture obtained by the separation. However, it is preferred that separation is performed so as to be contained in the remaining mixture obtained by separation, thus recovering as a mixture containing water. Here, the main component in the mixture containing propyne and propadiene as main components means that the total content of propyne and propadiene in the mixture is 50% by weight or more based on the total content of propyne, propadiene, water, and acetone in the mixture.

The separation method in the propyne/propadiene separation step is preferably a distillation method in view of processing efficiency and running cost. If necessary, the separation method may be used in combination with known methods such as absorption, membrane separation, adsorption separation, and extraction separation methods. There is no particular limitation on distillation apparatus, and it is possible to use, for example, a tray column, a packing column, a thin film evaporator, a flash evaporator, a centrifugal distillation apparatus, and the like. Of these, a tray column and a packing column are preferable. Distillation may be performed in a continuous manner, a batchwise manner, or a semibatchwise manner, and preferably a continuous manner. The operation pressure of distillation is preferably 50 to 1,000 kPa (absolute pressure). The operation temperature (temperature of column bottom of distillation column) depends on the operation pressure, and is preferably 40 to 180° C. The distillation is preferably performed in the form of rectification in which a distillation apparatus is provided with a capacitor and a gas from the column top of the distillation column is cooled, and then at least a part of the obtained condensate is returned to the column top. The distillation apparatus may be provided with a reboiler for partially vaporizing the liquid near the column bottom. When using a tray column or a packing column as a distillation apparatus, the number of theoretical stages is preferably 2 to 50 stages, and more preferably 5 to 30 stages. When a tray column is used as a distillation apparatus, there is no particular limitation on tray, and known stages can be used and, for example, a sieve tray, a ripple tray, a bubble cap tray, and the like can be used. When a packing column is used as a distillation apparatus, there is no particular limitation on packing material, and known packing materials can be used. It is possible to use, for example, Raschig ring, Lessing ring, Dixonpacking, Pall ring, saddle, Sulzer packing, Mellapak, and the like. In the case of performing separation by distillation, a mixture containing propyne and propadiene as main components is preferably allowed to flow out from the column top of a distillation apparatus to thereby separate a mixture containing propyne and propadiene as main components from the reaction mixture obtained in the dehydration reaction step, and then conditions are set so as to recover a mixture containing the unreacted acetone and water from the column bottom of the distillation apparatus.

When separation in the propyne/propadiene separation step is performed by distillation, the temperature of the reaction mixture obtained in the dehydration reaction step is preferably adjusted before distillation. There is no particular limitation on temperature controller, and a multi-tubular heat exchanger can be used. The reaction mixture obtained in the dehydration reaction step is preferably distilled after adjusting the temperature within a range of −50 to 180° C. The pressure during the adjustment of the temperature is preferably 50 to 1,200 kPa (absolute pressure). After the adjustment of the temperature, the mixture is subjected to distillation in a state of a gas, a liquid, or a mixture thereof. When the mixture after the adjustment of the temperature is a mixture of a gas and a liquid and the liquid contains water as a main component, and also the concentration of propyne and propadiene is low, only a gas obtained by gas-liquid separation of the mixture may be subjected to distillation.

When a mixture containing the unreacted acetone is obtained by separation in the propyne/propadiene separation step in the present invention, it is preferred to include an acetone circulation step of supplying at least a part of acetone contained in a mixture containing the unreacted acetone obtained in the propyne/propadiene separation step to the above-mentioned dehydration reaction step from the viewpoint of an improvement in economy due to recycling of the starting material. The supply may be performed by subjecting a mixture containing the unreacted acetone obtained by the propyne/propadiene separation step to a treatment such as distillation, diffusion, or the like to thereby separate the mixture containing acetone as a main component, and then supplying at least a part of the mixture. When water is further contained in the mixture containing the unreacted acetone, at least a part of acetone contained in the mixture obtained after separation of water is preferably subjected to the dehydration reaction step. It is possible to perform separation between acetone and water by distillation.

The propyne purification step of the present invention is a step of separating a mixture containing propyne and propadiene as main components separated in the propyne/propadiene separation step into a liquid, a gas, or a gas-liquid mixture containing propyne as a main component, and a liquid, a gas, or a gas-liquid mixture containing propadiene as a main component.

Examples of the method in which the mixture containing propyne and propadiene as main components obtained in the propyne/propadiene separation step is separated into a liquid, a gas, or a gas-liquid mixture containing propyne as a main component, and a liquid, a gas, or a gas-liquid mixture containing propadiene as a main component include absorption, distillation, extractive distillation, and adsorption methods. Examples of the absorption method include a method in which a mixture containing propyne and propadiene as main components is brought into contact with a solvent. An absorption column is used, for example, for the contact. It is possible to use, as the absorption column, a packing column, a wetted wall column, a spray column, a cyclone scrubber, a bubble column, a bubble agitation tank, a tray column (bubble-cap column, perforated tray column), a foam separation column, and the like. There is no particular limitation on pressure in absorption, and the pressure is preferably 50 to 900 kPa (absolute pressure). There is no particular limitation on temperature, and the temperature is preferably −50 to 100° C. When the mixture obtained in the propyne/propadiene separation step contains non-cohesive or volatile by-produced components, and an inert component to be introduced from the dehydration reaction step, these components can be separated and recovered by circulating in a solvent, followed by absorption of propyne and propadiene in the solvent. The solvent may be a solvent which dissolves propyne and propadiene and, for example, it is possible to use N,N-dimethylformamide.

The extractive distillation can be performed in accordance with the methods disclosed, for example, in EP 392601 A, EP 533291 A, and EP 533628 A. There is no particular limitation on the solvent to be used for extractive distillation as long as there is a difference in solubility between propyne and propadiene. From the viewpoint of propyne separability, economy, chemical stability, and industrial availability, N,N-dimethylformamide is preferable. When absorption is performed in a previous stage of extractive distillation, a solvent to be used for absorption can be used as a solvent for extractive distillation as it is. When using a solvent in which propyne has higher solubility than that of propadiene such as N,N-dimethylformamide, a liquid, gas, or gas-liquid mixture containing propadiene as a main component is recovered from the column top and a solution containing propyne and solvent as main components is recovered from the column bottom in an extractive distillation column. When the solution containing propyne and solvent as main components contains propadiene, it is possible to separately provide a propadiene diffusion step of supplying the solution to a stripping column and heating the solution to diffuse a gas containing propadiene as a main component and obtain a solution containing propyne as a main component from the column bottom. The solution containing propyne and solvent as main components obtained by the extractive distillation may be further distillated and such distillation enables separation into a liquid, gas, or gas-liquid mixture containing propyne as a main component and a solvent to obtain high-concentration propyne. The solvent to be recovered by the distillation can be recycled to the absorption or extractive distillation after being appropriately purified. Here, the main component in the liquid, gas, or gas-liquid mixture containing propyne as a main component means that the amount of propyne contained in the liquid, gas or gas-liquid mixture is more than 50% by weight based on the total amount of propyne and propadiene contained in the liquid, gas or gas-liquid mixture, and the main component in the liquid, gas, or gas-liquid mixture containing propadiene as a main component means that the amount of propadiene contained in the liquid, gas or gas-liquid mixture is more than 50% by weight based on the total amount of propyne and propadiene. The content of propadiene in the liquid, gas, or gas-liquid mixture containing propyne as a main component to be subjected to the carbonylation reaction step is preferably 50 ppm by weight or less based on the total content of propyne and propadiene.

The liquid, gas, or gas-liquid mixture containing propadiene as a main component obtained in the propyne purification step, or the gas containing propadiene as a main component obtained in the propadiene diffusion step may be subjected to an isomerization reaction step in which an isomerization reaction is performed in the presence of an isomerization catalyst to obtain a mixture containing propyne and propadiene as main components.

There is no particular limitation on ratio of propyne and propadiene contained in starting materials to be subjected to the isomerization reaction step, and a weight ratio of propyne/propadiene is usually 1 or less. The weight ratio of propyne/propadiene of an isomerization reactant to be taken out from the reactor depends on the reaction temperature and the retention time to the reactor, and is usually 3 or more, and preferably 5 or more. The mixture containing propyne and propadiene as main components obtained in the isomerization reaction step is preferably supplied to the propyne purification step from the viewpoint of economy. Examples of the isomerization catalyst include a solid acid catalyst and a solid base catalyst, and the solid base catalyst is preferable from the viewpoint of isomerizability. Examples of the solid acid catalyst include alumina, silica-alumina, titania, zeolite, heteropoly acid, and sulfate radical zirconia. Examples of the solid base catalyst include a catalyst in which at least one selected from the group consisting of alkali metals and alkali metal compounds is supported on a carrier. Of these catalysts, a catalyst in which an alkali metal compound is supported on a carrier is preferable. In the catalyst in which at least one selected from the group consisting of alkali metals and alkali metal compounds is supported on carrier, examples of alkali metals include potassium and cesium. Examples of alkali metal compounds include oxides of alkali metals, halides of alkali metals, hydroxides of alkali metals, carbonates of alkali metals, nitrates of alkali metals, hydrides of alkali metals, alkali metal alkoxides, and acetates ofalkali metals. If necessary, two or more alkali metal compounds may be supported on a carrier. Of the exemplified alkali metal compounds, potassium compounds are preferable from the viewpoint of isomerizability. In the catalyst in which at least one selected from the group consisting of alkali metals and alkali metal compounds is supported on a carrier, examples of the carrier include silica and magnesia. Of these compounds, alumina is preferable from the viewpoint of isomerizability. Of these alumina, γ-alumina is preferable.

In the isomerization reaction step, when using, as the isomerization catalyst, a catalyst in which at least one selected from the group consisting of alkali metals and alkali metal compounds is supported on a carrier, the carrier preferably has an average pore diameter of 4.5 nm or more. The upper limit value of the average pore diameter is preferably 15 nm or less, and more preferably 10 nm or less. The average pore diameter is the value obtained by measuring using a mercury penetration method. The pore volume of the carrier is preferably 0.40 mL/g or more, and more preferably 0.50 mL/g or more. The upper limit value of the pore volume is preferably 2.5 mL/g or less, and more preferably 1.5 mL/g or less. The pore volume is the value obtained by measuring using a mercury penetration method. The specific surface area of the carrier is preferably 100 $m^2/g$ or more from the viewpoint of the supporting amount of at least one selected from the group consisting of alkali metals and alkali metal compounds. The specific surface area is the value obtained by measuring using a nitrogen adsorption method (BET method), and usually the value obtained by measuring using a BET one point method. It is preferred to use, as the catalyst in which at least one selected from the group consisting of alkali metals and alkali metal compounds is supported on a carrier, a catalyst obtained by calcining after supporting at least one selected from the group consisting of alkali metals and alkali metal compounds on a carrier.

The isomerization reaction in the isomerization reaction step may be performed in a batchwise manner, a semibatchwise manner, or a continuous manner. The reaction in a continuous manner may be performed under either a liquid phase condition or a vapor phase condition, and the reaction can be carried out, for example, by a fixed bed flow system. The temperature in isomerization is usually −30 to 150° C., and preferably 0 to 100° C. in the case of a liquid phase reaction. The temperature in isomerization is usually 0 to 600° C., and preferably 100 to 400° C., in the case of a vapor phase reaction. The reaction pressure in isomerization is usually 0.1 to 10 MPa in the case of a liquid phase reaction, or usually 0.001 to 1 MPa in the case of a vapor phase reaction.

The amount of the catalyst used in the isomerization reaction is preferably 0.0001 to 0.1 mol, and more preferably, 0.001 to 0.05 mol, in terms of an alkali metal element in the catalyst, based on 1 mol of propadiene.

In the isomerization reaction, a diluent and/or a solvent may be used. Examples of the diluent and/or solvent include inorganic gases such as helium, nitrogen, and argon; aliphatic hydrocarbons such as methane, ethane, propane, butane, pentane, hexane, and octane; alicyclic hydrocarbons such as cyclopentane and cyclohexane; aromatic hydrocarbons such as benzene, toluene, and xylene; and aprotic polar solvents such as N,N-dimethylformamide and N,N-dimethylacetamide. If necessary, two or more diluents and/or solvents can also be used.

The isomerization reaction is preferably performed under the condition in which water and carbon dioxide do not substantially exist. Whereby, it is possible to suppress activity of the catalyst from deteriorating.

The carbonylation reaction step of the present invention is a step which a liquid, gas, or gas-liquid mixture containing propyne as a main component obtained in the propyne purification step is brought into contact with carbon monoxide and an alcohol having 1 to 3 carbon atoms in the presence of a catalyst containing at least one selected from the group consisting of Group 8 metal elements, Group 9 metal elements, and Group 10 metal elements to obtain a methacrylic acid ester.

Examples of the catalyst containing at least one selected from the group consisting of Group 8 metal elements, Group 9 metal elements, and Group 10 metal elements to be used in the carbonylation reaction step include a catalyst containing a metal element itself of at least one selected from the group consisting of Group 8 metal elements, Group 9 metal elements, and Group 10 metal elements; a catalyst containing a metal element of at least one selected from the group consisting of Group 8 metal elements, Group 9 metal elements, and Group 10 metal elements in the form of a compound; a catalyst containing a metal element itself of at least one selected from the group consisting of Group 8 metal elements, Group 9 metal elements, and Group 10 metal elements, and compounds of a metal elements of at least one selected from the group consisting of Group 8 metal elements, Group 9 metal elements, and Group 10 metal elements. Examples of the Group 8 metal elements include Fe, Ru, and Os; examples of the Group 9 metal elements include Co, Rh, and Ir; and examples of the Group 10 metal elements include Ni, Pd, and Pt. The catalyst is preferably a catalyst containing Group 10 metal elements, and more preferably a catalyst containing the compound of Group 10 metal elements. Examples of the compound of Group 10 metal elements include nickel compounds, palladium compounds, and platinum compounds, and preferably palladium compounds. Examples of palladium compounds include palladium acetylacetonate, tetrakis(triphenylphosphine)palladium, bis (triphenylphosphine)palladium acetate, palladium acetate, trifluoropalladium acetate, palladium trifluoromethanesulfonate, palladium sulfate, palladium chloride, and mixtures thereof. Palladium compounds more preferably include palladium acetylacetonate, tetrakis(triphenylphosphine)palladium, bis (triphenylphosphine)palladium acetate, palladium acetate, trifluoropalladium acetate, palladium trifluoromethanesulfonate, palladium sulfate, and mixtures thereof, and still more preferably palladium acetate. The amount of at least one selected from the group consisting of Group 8 metal elements, Group 9 metal elements, and Group 10 metal elements to be used is 1/200,000 mol or less, and preferably within a range of 1/1,000,000 to 1/200,000 mol, based on 1 mol of propyne. That is, the amount of propyne to be used is 200,000 mol or more, and preferably within a range of 200,000 to 1,000,000 mol, based on 1 mol of at least one selected from the group consisting of Group 8 metal elements, Group 9 metal elements, and Group 10 metal elements. When the catalyst contains two or more metal elements, the total amount thereof to be used may be within the above range.

It is preferred that the catalyst to be used in the carbonylation reaction step further contains protonic acid and a phosphine compound. Specific examples of the protonic acid and phosphine compound include those disclosed in JP 2010-120921 A, and they can be used in accordance with the method disclosed in the publication. An amine compound may be further used as the catalyst, though it is not indispensable. Specific examples of the amine compound include those disclosed in JP 2010-120921 A, and the amine compound can be used in accordance with the method disclosed in the publication.

Specific examples of the alcohol having 1 to 3 carbon atoms to be used in the carbonylation reaction step include methanol, ethanol, 1-propanol, 2-propanol, and ethylene glycol. Examples of preferred embodiment include embodiments in which methyl methacrylate is produced by reacting with methanol. The amount of the alcohol to be used may be appropriately adjusted according to the water content in the alcohol so that water existing in the reaction system becomes preferably 40,000 mol or less, more preferably 4,000 mol or less, still more preferably 1,000 mol or less, and particularly preferably 500 mol or less, based on 1 mol of at least one selected from the group consisting of Group 8 metal elements, Group 9 metal elements, and Group 10 metal elements contained in the catalyst existing in the reaction system. There is no particular limitation on the lower limit value, and it is usually 10 mol or more. When the catalyst contains two or more metal elements, the content of water existing in the reaction system may be within the above range based on the total amount thereof. The content of water existing in the reaction system may be adjusted by controlling the water content in the alcohol having 1 to 3 carbon atoms. The content of water in the alcohol having 1 to 3 carbon atoms can be adjusted, for example, by treating the alcohol with desiccants such as molecular sieve, alumina, silica gel, $Na_2SO_4$, $MgSO_4$, $CuSO_4$, $P_2O_5$, $CaH_2$, BaO, and CaO, and reducing the water content in the alcohol having 1 to 3 carbon atoms. The water content in the alcohol is preferably 1,000 ppm by weight or less, more preferably 750 ppm by weight or less, still more preferably 500 ppm by weight or less, and particularly preferably 100 ppm by weight or less. The amount of the alcohol to be used is preferably 1 mol or more, and more preferably 1 to 5 mol, based on 1 mol of propyne.

In the carbonylation reaction step, use of the solvent is not indispensable. It is preferred to lower partial pressure of propyne/propadiene. Suitably, an excess amount of an alcohol having 1 to 3 carbon atoms is used in place of the solvent. Separately, it is also possible to use another solvent. Specific examples of usable solvent include those disclosed in JP 2010-120921 A, and the solvent can be used in accordance with the method disclosed in the publication. From the viewpoint of ease of recycling, it is preferred to use an excess amount of an alcohol having 1 to 3 carbon atoms in place of the solvent.

There is no particular limitation on the contact temperature in the carbonylation reaction step, and the carbonylation reaction step is preferably carried out within a range of 20 to 100° C. The contact time varies depending on the amount of the catalyst, and conditions such as temperature and pressure, and is usually 0.5 to 48 hours. There is no particular limitation on the contact pressure, and it is preferably within a range of 0.5 to 10 MPaG (gauge pressure), and more preferably 1.0 to 7 MPaG (gauge pressure). At this time, there is no particular limitation on carbon monoxide partial pressure, and it is preferably within a range of 0.5 to 10 MPaG (gauge pressure), and more preferably 1.0 to 7 MPaG (gauge pressure). The liquid or gas containing propyne as a main component may contain propadiene and other impurities, as long as the reaction is not drastically inhibited. Specific examples of these impurities include butadiene, propylene, butene, propane, carbon monoxide, and carbon dioxide. Carbon monoxide to be used in the present invention may contain, in addition to pure carbon monoxide, an inert gas, which is inert relative to the catalyst and propyne, such as nitrogen, helium, carbon dioxide, or argon. There is no particular limitation on the embodiment of the reaction of the present invention, and the reaction may be performed either in a batchwise or continuous manner.

In the carbonylation reaction step, it is preferred that a part or the whole of impurities entrained by the liquid, gas, or gas-liquid mixture containing propyne as a main component obtained in the propyne purification step, the unreacted carbon monoxide, the inert gas entrained by carbon monoxide, and the like is appropriately discharged out of the system from the viewpoint of avoiding accumulation in the system.

Specific examples of the methacrylic acid ester obtained in the carbonylation reaction step include methacrylic acid esters such as methyl methacrylate, ethyl methacrylate, n-propyl methacrylate, isopropyl methacrylate, and 2-hydroxyethyl methacrylate.

It is preferred that the production method of the present invention includes the following methacrylic acid ester purification step from the viewpoint of improving quality of the methacrylic acid ester and economy of recycle of the starting material.

The methacrylic acid ester purification step is a step of recovering the unreacted propyne and the unreacted alcohol having 1 to 3 carbon atoms from the reaction mixture containing the methacrylic acid ester obtained in the carbonylation reaction step, the unreacted propyne, and the unreacted alcohol having 1 to 3 carbon atoms, and also purifying the methacrylic acid ester.

The reaction mixture produced from the carbonylation reaction step contains, as main components, a methacrylic acid ester, a crotonic acid ester, the unreacted alcohol having 1 to 3 carbon atoms, the unreacted propyne, and a catalyst.

When the carbonylation reaction step was performed by supplying an excess amount of carbon monoxide relative to propyne and, after the reaction, the unreacted carbon monoxide is also recovered and at least apart of the carbon monoxide thus recovered may be recycled in the carbonylation reaction step. In order to simplify the recycle process, recycling of carbon monoxide is preferably omitted by carrying out the carbonylation reaction step so as not to produce the unreacted carbon monoxide using a method in which carbon monoxide is supplied in the system in only an amount which enables conversion into a methacrylic acid ester by reaction in one pass to thereby lengthen the contact time. The crotonic acid ester contained in the reaction mixture is by-products and the product component must be removed out of the system. At least a part of an alcohol having 1 to 3 carbon atoms, propyne, and a catalyst is preferably recycled. It is particularly preferred that the production method of the present invention includes an alcohol circulation step of supplying at least apart of an alcohol having 1 to 3 carbon atoms obtained in the methacrylic acid ester purification step to the carbonylation reaction step.

There is no particular limitation on the separation method of propyne and an alcohol having 1 to 3 carbon atoms from the reaction mixture in the methacrylic acid ester purification step. Examples of the separation method from the reaction mixture include a gas diffusion operation, a distillation operation, an extraction operation, or combinations thereof. Of these, distillation utilizing a boiling point difference, or separation by extractive distillation utilizing a solubility difference in an extraction solvent is advantageous. For example, first, a component having a vapor pressure higher than that of the methacrylic acid ester is separated by distillation. The component having a vapor pressure higher than that of the methacrylic acid ester is, for example, propyne or an alcohol having 1 to 3 carbon atoms. Thereafter, the methacrylic acid ester is distilled and a mixed solution containing a crotonic acid ester and a catalyst as main components remains on the column bottom. The mixed solution containing a crotonic acid ester and a catalyst as main components may be discharged. However, since at least one selected from the group consisting of Group 8 metal elements, Group 9 metal elements, and Group 10 metal elements is usually expensive, it is preferred to recycle the mixed solution. There is no particular limitation on the recycling method, and it is usually a method in which only an amount corresponding to that of the crotonic acid ester generated in the carbonylation reaction step is discharged out of the system from the mixture containing a crotonic acid ester and a catalyst as main components, and then the rest is recycled to the carbonylation reaction step. The temperature of the methacrylic acid ester purification step is preferably 100° C. or lower from the viewpoint of polymerization inhibition of the methacrylic acid ester. A polymerization inhibitor may be added. Examples of the polymerization inhibitor include hydroquinone.

In the alcohol circulation step, when an alcohol having 1 to 3 carbon atoms obtained in the methacrylic acid ester purification step is recovered as a mixture, at least a part of the alcohol may be supplied to the carbonylation reaction step after converting into a high concentration alcohol having 1 to 3 carbon atoms by a purification operation such as distillation.

DESCRIPTION OF REFERENCE NUMERALS

A: Dehydration reaction step
B: Propyne/propadiene separation step
C: Propyne purification step
D: Acetone circulation step
E: Isomerization reaction step
F: Carbonylation reaction step
G: Methacrylic acid ester purification step
H: Alcohol circulation step
1, 21, 41, 61, 81: Starting material supply line
2, 31, 44, 70, 87: Oxygen-containing gas line
3, 29, 48: Inert purge gas line
4: Reacted gas takeout line
5, 42, 62: Preheater
6, 23, 43, 63, 86: Combustion gas supply line
7, 24, 64: Combustion air supply line
8, 65: Preheater waste gas line
9: Preheated starting material gas supply line
10, 45: Heat insulation-type fixed bed reactor
11, 27, 46: Solid catalyst layer
12, 28, 47, 68, 84: Reaction mixture takeout line
22: Heating furnace
25: Heating furnace waste gas line
26: Fixed bed reaction tube
30, 51, 74, 89: Regenerated off-gas line
49: Heating furnace for catalyst regeneration
50: Catalyst regenerated gas supply line
66: Heat insulation-type moving bed reactor
67: Catalyst moving layer
69: Catalyst regenerator
71: Supplementing catalyst supply line
72, 91: Regenerated catalyst transfer tube
73, 90: Used catalyst transfer tube
82: Reaction column
83: Cyclone
85: Catalyst transfer gas line
88: Regeneration column

EXAMPLES

Examples of the present invention will be described below, but the present invention is not limited thereto.

Example 1

When methyl methacrylate is produced using acetone, methanol, and carbon monoxide as starting materials, the production process can be carried out in the most suitable manner, for example, by flow in FIG. 1 and material balance in Table 1.

Acetone (fluid number 1) (647 kg/h) was supplied to a dehydration reaction step (A), together with 926 kg/h of a recycle fraction (fluid number 9) from an acetone circulation step (D) and then acetone is subjected to a dehydration reaction in the presence of a potassium hydroxide-supported silica catalyst to obtain 1,573 kg/h of a dehydration reaction mixture (fluid number 2) which contains 27.0% by weight in total of propyne and propadiene, and also contains the unreacted acetone, product water, by-products, and impurities in starting materials. The dehydration reaction mixture thus obtained is supplied to a propyne/propadiene separation step (B) and is partially condensed while cooling to thereby separate into 461 kg/h of a gas mixture (fluid number 3) containing propyne and propadiene as main components, and 1,112 kg/h of a liquid mixture (fluid number 4) containing water and acetone as main components. The gas mixture (fluid number 3) obtained in the propyne/propadiene separation step is supplied to a propyne purification step (C), and then separated into 23 kg/h of a gas mixture (fluid number 5) containing a low boiling component as a main component, 151 kg/h of a fraction (fluid number 6) containing propadiene as a main component, 406 kg/h of purified propyne (fluid number 7), and 32 kg/h of a fraction (fluid number 8) containing a high boiling component as a main component by cooling and distillation. The liquid mixture (fluid number 4) obtained in the propyne/propadiene separation step (B) is supplied an acetone circulation step (D) and then separated into 926 kg/h of a recycle fraction (fluid number 9) containing acetone as main component and 186 kg/h of water (fluid number 10) by distillation. The fraction (fluid number 6) containing propadiene as a main component obtained in the propyne purification step (C) is supplied to an isomerization reaction step (E) and then propadiene is subjected to an isomerization reaction in the presence of a potassium carbonate supported-alumina catalyst to obtain 151 kg/h of an isomerization reaction mixture (fluid number 11) containing propyne as a main component.

The purified propyne (fluid number 7) obtained in the propyne purification step (C) is supplied to a carbonylation reaction step (F), together with 322 kg/h of methanol (fluid number 12), 285 kg/h of carbon monoxide (fluid number 13), and 666 kg/h of a recycle fraction (fluid number 19) obtained in an alcohol circulation step (H), and then reacted in the presence of a palladium based catalyst to obtain 1,673 kg/h of a carbonylation reaction mixture (fluid number 14) which contains 63.1% by weight of methyl methacrylate and also contains the unreacted methanol, propyne, by-products, and impurities in starting materials, and also 5 kg/h of a gas mixture (fluid number 15) containing a low boiling component contained in starting materials as a main component is discharged. The carbonylation reaction mixture (fluid number 14) thus obtained is supplied to a methacrylic acid ester purification step (G), and then separated into 671 kg/h of a fraction (fluid number 16) containing methanol as a main component, 1,000 kg/h of purified methyl methacrylate (fluid number 17), and 2 kg/h of a fraction (fluid number 18) containing a high boiling component as a main component by distillation. The fraction containing mainly methanol obtained in the methacrylic acid ester purification step (G) is supplied to an alcohol circulation step (H), and then separated into 666 kg/h of a recycle fraction (fluid number 19) containing methanol as a main component and also containing propyne and methyl methacrylate, and 5 kg/h of a fraction (fluid number 20) containing impurities introduced from a carbonylation reaction starting material as a main component by distillation.

TABLE 1

| Fluid number | 1 | 2 | 3 | 4 | 5 | 6 | 7 | 8 | 9 | 10 |
|---|---|---|---|---|---|---|---|---|---|---|
| Mass flow rate (kg/h) | 647 | 1,573 | 461 | 1,112 | 23 | 151 | 406 | 32 | 926 | 186 |
| Weight percentage (% by weight) | | | | | | | | | | |
| Carbon monoxide | | | | | | | | | | |
| Propadiene | | 6.6 | 22.2 | 0.2 | 11.1 | 82.5 | 8 ppm | | 0.2 | |
| Propyne | | 20.4 | 66.7 | 1.2 | 18.9 | 17.5 | 99.2 | 1.3 | 1.4 | |
| Acetone | 99.7 | 57.7 | 1.0 | 81.1 | | | | 14.1 | 97.5 | 100 ppm |
| Methanol | | | | | | | | | | |
| Water | 0.3 | 12.3 | | 17.4 | | | | | 0.7 | 100.0 |
| Methyl methacrylate | | | | | | | | | | |
| Others | | 3.0 | 10.1 | 0.1 | 70.0 | | 0.8 | 84.6 | 0.2 | |
| Total | 100.0 | 100.0 | 100.0 | 100.0 | 100.0 | 100.0 | 100.0 | 100.0 | 100.0 | 100.0 |

| Fluid number | 11 | 12 | 13 | 14 | 15 | 16 | 17 | 18 | 19 | 20 |
|---|---|---|---|---|---|---|---|---|---|---|
| Mass flow rate (kg/h) | 151 | 322 | 285 | 1673 | 5 | 671 | 1000 | 2 | 666 | 5 |
| Weight percentage (% by weight) | | | | | | | | | | |
| Carbon monoxide | | | 99.2 | | 43.8 | | | | | |
| Propadiene | 16.5 | | | | | | | | | |
| Propyne | 83.5 | | | 2.6 | 6.2 | 6.5 | | | 6.4 | 17.1 |
| Acetone | | | | | | | | | | |
| Methanol | | 100.0 | | 34.1 | | 85.0 | 50 ppm | | 85.5 | 22.4 |
| Water | | 100 ppm | | | | | | 1.5 | | |
| Methyl methacrylate | | | | 63.1 | | 8.0 | 100.0 | 49.2 | 8.1 | |
| Others | | | 0.8 | 0.2 | 50.0 | 0.5 | | 49.3 | | 60.5 |
| Total | 100.0 | 100.0 | 100.0 | 100.0 | 100.0 | 100.0 | 100.0 | 100.0 | 100.0 | 100.0 |

Reference Example 1

<Production of Catalyst>

A silica powder [$SiO_2$, manufactured by Tosoh Silica Corporation, NIPSIL ER-R] was used as a carrier. The carrier (20.0 g) was impregnated with an aqueous solution prepared by mixing 4.6 g of a potassium silicate solution [manufactured by Wako Pure Chemical Industries, Ltd., an aqueous solution of $K_2O \cdot 3.9SiO_2$ ($SiO_2/K_2O=3.9$ [molar ratio]) $K_2O \cdot 3.9SiO_2$ content: 28.1% by weight] with 35.0 g of pure water, followed by air drying at 20 to 30° C. for 15 hours or more. The solid thus obtained was subjected to press molding and, after the temperature was raised to 200° C. from room temperature over 0.5 hour under an air flow, the molded body was calcined by retaining at the same temperature for 2 hours. Then, the calcined product thus obtained was pulverized into granules of 0.85 to 1.4 mm in diameter to obtain a catalyst (potassium silicate content: 6.1% by weight) in which potassium silicate is supported on silica.

<Catalyst Packing>

A reaction tube made of quartz provided with a thermometer protective tube having an outer diameter of 4 mm was packed with quartz wool as a partitioning agent at the lower portion having an inner diameter of 14 mm, packed with 7.1 mL of SiC, packed with quartz wool as a partitioning agent, packed with 2.4 g (volume of 6.3 mL) of the resulting catalyst, packed with quartz wool as a partitioning agent, and then packed with 12.7 mL of SiC.

<Dehydration Reaction>

While supplying a nitrogen gas into the reaction tube through an inlet of the reaction tube packed with the catalyst at a rate of 2.7 ml/minute, the pressure inside the reaction tube was reduced to 0.01 MPa or less using a diaphragm pump, and then the reaction tube was heated by an electric furnace, leading to temperature rise.

Liquid acetone (manufactured by Wako Pure Chemical Industries, Ltd.) was supplied through an inlet of the reaction tube by a pump and gasified [acetone gas supply rate: 34.2 ml/minute (0.092 mol/h), acetone concentration in supply gas: 92.7% by volume], and then a reaction was started under a reaction pressure of 0.008 MPa. A ratio (GHSV) of a whole gas flow rate to a catalyst volume was 351 h$^{-1}$. The value (ml/minute) indicating a supply rate of a gas is a value in terms of 0° C., 1 atom (101.325 kPa) unless otherwise specified.

After starting the reaction, the temperature of a catalyst layer was retained at 650° C.±8° C. At the point of time when 60 minutes have passed from starting of the reaction, a reactor outlet gas was collected by a gas-tight syringe and analyzed by gas chromatography with an FID detector. After packing a sampling group with the reactor outlet gas, each product was quantitatively determined by online analysis through gas chromatography with a TCD detector. A trap made of SUS connected to the reaction tube outlet was cooled in an ethanol/dry ice bath. After recovering acetone and a high boiling point component by condensation, the condensate thus obtained was analyzed by gas chromatography with an FID detector, and then acetone and a high boiling point component were quantitatively determined. The results are shown in Table 2.

Here, a conversion rate (%) of acetone was calculated using the following equation (i).

Conversion rate (%) of acetone=[b/(a+b)]×100     (i)

where
a: acetone flow rate (mol/h) in reactor outlet gas
b: total production rate (mol/h) of whole product in reaction tube outlet gas A selectivity (%) to each product was calculated using the following equation (ii).

Selectivity (%) to each product=[(production rate (mol/h) of each product in reactor outlet gas)/ (total production rate (mol/h) of whole product in reactor outlet gas)]×100     (ii)

The product as used herein means propyne, propadiene, methane, ethane, ethylene, acetylene, propylene, propane, isobutylene, 2-methyl-1-penten-3-yne, 2-hexen-4-yne, 4-methyl-3-penten-2-one, 4-methyl-4-penten-2-one, 2-methylfuran, methylcyclopentadiene, 3,5,5-trimethyl-2-cyclohexen-1-one, phenol, methylphenol, 3,5-dimethylphenol, carbon monoxide, and carbon dioxide.

TABLE 2

| | | Reference Example 1 |
|---|---|---|
| Catalyst | Support component | K$_2$O•3.9SiO$_2$ |
| | Support component content (% by weight) | 6.1 |
| | Carrier | SiO$_2$ |
| | Acetone concentration in supply gas (% by volume) | 92.7 |
| | Acetone conversion rate (%) | 50.1 |
| Selectivity (%) | Propyne | 68.1 |
| | Propadiene | 23.2 |
| | Methane | 1.7 |
| | Ethane | 0.0 |
| | Ethylene | 0.0 |
| | Acetylene | 0.0 |
| | Propylene | 0.3 |
| | Propane | 0.0 |
| | Isobutylene | 0.7 |
| | 2-Methyl-1-penten-3-yne and 2-hexen-4-yne | 0.8 |
| | 4-Methyl-3-penten-2-one and 4-methyl-4-penten-2-one | 0.2 |
| | 2-Methylfuran | 2.5 |
| | Carbon monoxide | 1.2 |
| | Carbon dioxide | 0.0 |
| | Others*) | 1.3 |
| | Total selectivity (%) to propyne and propadiene | 91.3 |

*)methylcyclopentadiene, 3,5,5-trimethyl-2-cyclohexen-1-one, phenol, methylphenol, and 3,5-dimethylphenol

INDUSTRIAL APPLICABILITY

According to the present invention, it is possible to provide a method for producing a methacrylic acid ester, which is less likely to receive location restrictions, and is also economically and industrially advantageous.

The invention claimed is:

1. A method for producing a methacrylic acid ester, which comprises the following steps:
   a dehydration reaction step: a step of having acetone undergo a dehydration reaction in the presence of a dehydration reaction catalyst to obtain a reaction mixture containing propyne, propadiene, and water;
   a propyne/propadiene separation step: a step of separating a mixture containing propyne and propadiene as main components from the reaction mixture obtained in the dehydration reaction step;
   a propyne purification step: a step of separating the mixture containing propyne and propadiene as main components separated in the propyne/propadiene separation step into a liquid, gas, or gas-liquid mixture containing propyne as a main component, and a liquid, gas, or gas-liquid mixture containing propadiene as a main component; and
   a carbonylation reaction step: a step of bringing the liquid, gas, or gas-liquid mixture containing propyne as a main component obtained in the propyne purification step into contact with carbon monoxide and an alcohol having 1 to 3 carbon atoms in the presence of a catalyst containing at least one selected from the group consisting of Group 8 metal elements, Group 9 metal elements, and Group 10 metal elements to obtain a methacrylic acid ester; and
   wherein the dehydration reaction catalyst is a catalyst containing silicon and at least one selected from the group consisting of Group 1 metal elements and Group 2 metal elements.

2. The method according to claim 1, wherein the reaction mixture in the dehydration reaction step further contains unreacted acetone, and in the propyne/propadiene separation step, a mixture containing the unreacted acetone is obtained by separating the mixture containing propyne and propadiene as main components.

3. The method according to claim 2, further comprising the following step:
   an acetone circulation step: a step of supplying at least a part of acetone contained in the mixture containing the unreacted acetone obtained in the propyne/propadiene separation step to the dehydration reaction step.

4. The method according to claim 1, further comprising the following step:
   an isomerization reaction step: a step of isomerizing the liquid, gas, or gas-liquid mixture containing propadiene as a main component obtained in the propyne purification step in the presence of an isomerization catalyst to obtain a mixture containing propyne and propadiene as main components.

5. The method according to claim 1, further comprising the following step:
   a methacrylic acid ester purification step: a step of recovering propyne and an alcohol having 1 to 3 carbon atoms from the reaction mixture containing the methacrylic acid ester obtained in the carbonylation reaction step, the unreacted propyne, and the unreacted alcohol having 1 to 3 carbon atoms, and also purifying the methacrylic acid ester.

6. The method according to claim 5, further comprising the following step:
   an alcohol circulation step: a step of supplying at least a part of the alcohol having 1 to 3 carbon atoms obtained in the methacrylic acid ester purification step to the carbonylation reaction step.

\* \* \* \* \*